United States Patent [19]

Miyasaka et al.

[11] 4,399,282
[45] Aug. 16, 1983

[54] CAMPTOTHECIN DERIVATIVES

[75] Inventors: Tadashi Miyasaka, Yokohama; Masahiko Mutai, Higashiyamato; Seigo Sawada, Tokyo; Kenichiro Nokata, Mitaka; Hisao Hagiwara, Amagasaki, all of Japan

[73] Assignee: Kabushiki Kaisha Yakult Honsha, Tokyo, Japan

[21] Appl. No.: 166,953

[22] Filed: Jul. 8, 1980

[30] Foreign Application Priority Data

Jul. 10, 1979 [JP] Japan .................................. 54-86410
Jul. 10, 1979 [JP] Japan .................................. 54-86411
Jul. 10, 1979 [JP] Japan .................................. 54-86412
Jul. 10, 1979 [JP] Japan .................................. 54-86413
May 9, 1980 [JP] Japan .................................. 55-60736

[51] Int. Cl.³ .................. C07D 491/147; A61K 31/47
[52] U.S. Cl. ..................................... 546/48; 424/258
[58] Field of Search ......................................... 546/48

[56] References Cited

U.S. PATENT DOCUMENTS 3,894,029  7/1975  Winterfeldt et al. .................. 546/48
4,031,098  6/1977  Sugasawa ............................. 546/48

OTHER PUBLICATIONS

Baxmann et al., Chem. Ber., 111, 3403-3411 (1978).
Lown et al., Biochem. Pharmacol. 1980, 29(6), pp. 905-915 (6/80), Chemical Abstract, vol. 93, 61075 (1980).

Primary Examiner—Donald G. Daus
Assistant Examiner—Diana G. Rivers
Attorney, Agent, or Firm—Birch, Stewart, Kolasch & Birch

[57] ABSTRACT

New camptothecin derivatives possessing either or both of high anti-tumor activity and slight toxicity, represented by the general formula:

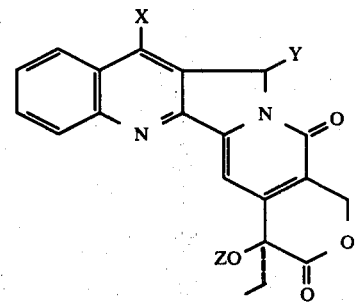

wherein X is H, $CH_2OH$, COOH, an alkyl group, an aralkyl group or the grouping $CH_2OR^1$ or $COOR^2$ wherein $R^1$ is an alkyl group or an acyl group and $R^2$ is a lower alkyl group, Y is H, OH or the grouping $OR^3$ wherein $R^3$ is a lower alkyl group or an acyl group, and Z is H or an acyl group, with the proviso that when X is $CH_2OH$, an alkyl group or an aralkyl group, both Y and Z are H, that when X is the grouping $CH_2OR^1$ or $COOR^2$, Y is H, that when Y is OH, both X and Z are H, and that when Y is the grouping $OR^3$, X is H, and water-soluble alkali metal salts thereof. These camptothecin derivatives are prepared by treating camptothecin with sulfuric acid and a persulfate or with sulfuric acid and a peroxide, if necessary, with an organic compound corresponding to the organic moiety of the substituent to be introduced directly into camptothecin, in an aqueous medium in the presence or absence of a transition metal ion, and optionally treating the resultant products, if necessary, after oxidation of the introduced substituent, with an alkylating agent or an acylating agent.

40 Claims, No Drawings

CAMPTOTHECIN DERIVATIVES

BACKGROUND OF THE INVENTION

1. Field of the Invention

This invention relates to new derivatives of camptothecin, an alkaloid possessing anti-tumor activity (including carcinostatic activity), and to processes for preparation of such derivatives. More particularly, this invention relates to new camptothecin derivatives bearing hydroxy or a functionally converted hydroxy substituent in the 5-position or an organic carbon substituent in the 7-position thereof and possessing at least one of strong anti-tumor activity and low toxicity as well as processes for the preparation of such derivatives.

2. Description of the Prior Arts

Camptothecin is a cytotoxic alkaloid, isolated first by Wall and his co-workers [J.Am. Chem. Soc. 88(1966), 3888] from leaves and barks of *Camptotheca accuminata* (NYSSACEAE), a plant native to China, which has a pentacyclic structure consisting of a fused ring system of quinoline (rings A and B), pyrroline (ring C), α-pyridone (ring D) and a six-membered lactone (ring E) and displays dextro-rotation due to the S-configuration of a tertiary hydroxy group in the 20-position. Earlier reports on the carcinostatic activity of camptothecin based on inhibitory activity toward an experimentally transplanted carcinoma such as leukemia L-1210 in mice or Walker 256 tumor in rats [Chem. Rev. 23(1973), 385; Cancer Treat. Rep., 60(1967), 1007] stimulated synthetical researches on camptothecin, but the subsequent biological evaluation in the reports indicated that this compound is highly toxic and consequently unusable as a chemotherapeutic agent. Because of high toxicity, camptothecin itself is not utilized at present for clinical treatments except in China, but this compound is still one of the most potent substances with antitumor activity and is thus regarded as important in the aspect of a biological reagent capable of inhibiting selectively the biosynthesis of ribosomal and messenger RNA's without disturbing the biosynthesis of mitochondrial, 4S or 5S RNA's [Nature (London), New Biol., 237(1972), 144].

Such earlier reports on the significant antitumor activity of camptothecin stimulated intensive interest in the total syntheses and chemical modifications of camptothecin. Many papers describe the syntheses of dl-camptothecin, its intermediate derivatives, and (+)-20(S)-camptothecin; synthesis of (+)-20(S)-camptothecin (Dextro-rotary) is reported by E. J. Corey et al., in J. Am. Chem. Soc. 40 2140 (1975). In addition, synthesis of dl-camptothecin is reported, for example, by J. C. Bradley et al., in J. Org. Chem. 41,699(1976) and by H. G. M. Walraven et al., in Tetrahedron 36, 321 (1980), the latter being a report on the latest synthesis of camptothecin. The natural camptothecin isolated from *Camptotheca accuminata* is known to be in the d-form. However, none of these reports refer to chemical modification of the original structure of camptothecin from the standpoint of chemotherapeutic usage. The chemical modifications so far reported are mainly concerned with the rings D and/or E of camptothecin, but the results of such modifications have revealed only failure in maintaining expected carcinostatic activity and poor improvement in toxicity [J. Med. Chem., 19(1976), 675].

From the chemotherapeutic point of view, it is of importance that the chemical modifications of camptothecin should be restricted in the rings A, B and C without effecting any serious change in the whole skeletal structure, especially in the rings D and E of the natural camptothecin, the latter rings D and E being conceivable to be one of the essential structural elements for the expression of the above mentioned biological activity. Functionalization of a moiety containing the rings A, B and C is little known, except for nitration of camptothecin in concentrated sulfuric acid under severe conditions conducted in China to obtain 12-nitrocamptothecin after troublesome separation treatments from other products. This 12-nitro derivative is then reduced to the corresponding 12-amino derivative which is further subjected to diazotization and subsequent hydrolysis or a Sandmeyer reaction to introduce a hydroxy group, chlorine atom, cyano group or carboxyl group into the 12-position of camptothecin [P. Pei-chuang et al.; Hau Hsueh Hsueh Pao, 33 (1975), 71; Chem. Abstr., 84 (1976), 115629p]. According to this method, however, it takes four steps to prepare the 12-cyano derivative and five steps to prepare the 12-carboxy derivative from the starting natural camptothecin. Except for this method wherein a number of troublesome steps are required for introducing a functional substituent into the 12-position of camptothecin, there has not yet been known heretofore any chemical modification for introducing a functional substituent in the ring A, B and/or C. The reason why introduction of a substituent into the ring A, B and/or C of camptothecin is extremely difficult is probably ascribable to poor solubility of camptothecin in ordinary organic solvents and to the nature of a nitrogen-containing heterocyclic ring which refuses an ionic reaction, especially the so-called electrophilic reaction conventionally carried out on aromatic rings, such as the Friedel-Crafts reaction, Vilsmeier-Haack reaction or other alkylation or acylation reactions.

Thus, there is still a great demand in this art for developing new derivatives of camptothecin possessing at least one of high anti-tumor activity and very weak toxicity by chemically modifying natural camptothecin on its ring A, B and/or C in one step without effecting any change in the structure of the rings D and E which are regarded to be indispensable for exhibiting the physiological activity.

BRIEF SUMMARY OF THE INVENTION

Accordingly, it is an object of the present invention to provide new camptothecin derivatives which are effective antitumor agents especially useful for both injection and oral administration.

It is another object of the present invention to provide new camptothecin derivatives which are strong in anti-tumor activity and possess good absorbability in the living body with very low toxicity.

It is still another object of the present invention to provide processes for the preparation of the new camptothecin derivatives.

It is a further object of the present invention to provide new means for introducing subtituents into the ring B or C of camptothecin without any modifications of the structure of the rings D and E of camptothecin.

It is still a further object of the present invention to provide the use of the new camptothecin derivatives as anti-tumor agents.

Other objects, features and advantages of the present invention will become apparent more fully from the following description.

DETAILED DESCRIPTION OF THE INVENTION

With an attempt to synthesize new camptothecin derivatives while maintaining the inherent anti-tumor activity with extremely reduced toxicity, the present inventors have conducted research for replacing any of the hydrogen atoms existing in the rings A, B and C with a substituent other than the hydrogen atom, paying careful attention to the replacement lest any change should occur in the structure of the rings D and E which are regarded to the indispensable for exhibiting the physiological activity of camptothecin. As a result of the present inventors' extensive research, it has been found surprisingly that a hydroxy group can be introduced into the 5-position and various organic groups can be introduced into the 7-position of camptothecin while keeping the rings D and E unchanged, when a radical substitution reaction in place of the conventionally employed ionic reactions is applied to camptothecin in a dilute aqueous acidic solution. The present invention which established a general method for introducing a functional substituent into a specific position of camptothecin is based on the above finding. Thus, it now becomes possible for the first time to prepare a series of new camptothecin derivatives in one step by introducing a functional substituent into the 7-position in the ring B and into the 5-position in the ring C while keeping the fundamental skeletal structure of the rings A, B, C, D and E and the functional groups therein unchanged during the substitution reaction.

In accordance with one embodiment of the present invention, there are provided new camptothecin derivatives of the general formula:

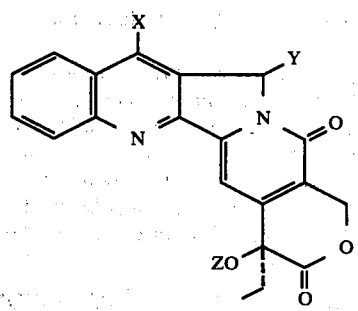

[I]

wherein X is H, CH$_2$OH, COOH, an alkyl group, an aralkyl group or the grouping CH$_2$OR$^1$ or COOR$^2$ where R$^1$ is an alkyl group or an acyl group and R$^2$ is a lower alkyl group, Y is H, OH or the grouping OR$^3$ where R$^3$ is a lower alkyl group or an acyl group, and Z is H or an acyl group, with the proviso that when X is CH$_2$OH, an alkyl group or an aralkyl group, both Y and Z are H, that when X is the grouping CH$_2$OR$^1$ or COOR$^2$, Y is H, that when Y is OH, both X and Z are H, and that when Y stands for the grouping OR$^3$, X stands for H, as well as water-soluble alkali metal salts thereof.

When X and R$^1$ each represent an alkyl group, they may be the same or different and generally have 1–30 carbon atoms. In view of the availability of alkylating reactants, the alkyl group has preferably 1–18 carbon atoms. Preferable examples of the alkyl group include straight or branched chain alkyl groups with 1–18 carbon atoms, such as methyl, ethyl, n-propyl, isopropyl, n-butyl, isobutyl, tert-butyl, n-pentyl, isopentyl, n-hexyl, n-heptyl, n-octyl, 2-ethylhexyl, n-nonyl, n-decyl, undecyl, dodecyl, myristyl, heptadecyl and octadecyl groups. When the alkyl groups are branched, the branched chains may be combined together to form a cycloalkyl group, Illustrative of such cycloalkyl groups are, for example, cyclopentyl, cyclohexyl, cycloheptyl and cyclooctyl. When R$^2$ and R$^3$ each represent a lower alkyl group, they may also be the same or different and usually have 1–8 carbon atoms. As described above, both lower alkyl groups R$^2$ and R$^3$ may have straight or branched chains and in the latter case the branched chains may be combined together to form a cycloalkyl group. Preferable examples of the lower alkyl group include a straight or branched chain alkyl group with 1–4 carbon atoms, such as methyl, ethyl, n-propyl, isopropyl, n-butyl, isobutyl, tert-butyl and cyclopropyl groups. Preferable examples of the aralkyl group include benzyl, phenethyl, phenylpropyl and 1-naphthylmethyl.

In general, when the substituent X exists in the 7-position of the ring B, no substituent exists in the 5-position of the ring C, or in other words, Y is H. On the other hand, if the substituent Y exists in the 5-position of the ring C, no substituent exists in the 7-position of the ring B. When R$^1$ and R$^3$ and Z are each an acyl group, they are usually the same but may be different. The acyl group is derived from an aliphatic or aromatic carboxylic acid, a halogen-substituted homolog thereof and an aliphatic or aromatic sulfonic acid. Illustrative of the aliphatic and aromatic carboxylic acids and sulfonic acids are, for example, formic acid, acetic acid, propionic acid, butyric acid, isobutyric acid, valeric acid, caproic acid, caprylic acid, nonylic acid, decanoic acid, phenylacetic acid, phenylpropionic acid, succinic acid, trifluoroacetic acid, benzoic acid, methanesulfonic cid, ethanesulfonic acid, benzenesulfonic acid and p-toluenesulfonic acid.

The camptothecin derivatives of this invention possess excellent pharmacological properties improved in at least one of the anti-tumor activity and the toxicity properties. Illustrative of the typical camptothecin derivatives of the present invention are 7-hydroxymethylcamptothecin, 5-hydroxycamptothecin, 20-O-acetyl-7-acetoxymethylcamptothecin, 7-acetoxymethylcamptothecin, 7-succinoyloxymethylcamptothecin, 20-O-trifluoroacetyl-7-trifluoroacetoxymethylcamptothecin, 7-benzoyloxymethylcamptothecin, 7-propionyloxymethylcamptothecin, 7-butyryloxymethylcamptothecin, 7-caprylyloxymethylcamptothecin, 7-caproxymethylcamptothecin, 7-isovaleryloxymethylcamptothecin, 7-phenylacetoxymethylcamptothecin, camptothecin-7-carboxylic acid, ethyl camptothecin-7-carboxylate, 5-methoxycamptothecin, 5-butoxycamptothecin, 5-acetoxycamptothecin, 20-O-acetyl-5-acetoxycamptothecin, 5-benzoyloxycamptothecin, 7-methylcamptothecin, 7-ethylcamptothecin, 7-propylcamptothecin, 7-butylcamptothecin, 7-heptylcamptothecin, 7-nonylcamptothecin, 7-isobutylcamptothecin, 7-benzylcamptothecin, 7-β-phenethylcamptothecin, 7-isopropylcamptothecin and 7-cyclohexylcamptothecin.

The new camptothecin derivatives of the present invention are not only limited to those from the naturally occurring (+)-camptothecin but involve also those from the corresponding (−)- and dl-camptothecins synthetically obtained.

As camptothecin itself carries a lactone ring as ring E, this lactone ring is opened by the action of an alkaline reagent. Similary, when the camptothecin derivatives of the present invention are treated, for example, with an alkali metal hydroxide or carbonate in a conventional manner at room temperature or at an elevated temperature, the derivatives can be converted into the corresponding alkali metal salt such as the sodium, potassium or lithium salt. These salts are all water-soluble and are of course involved in the scope of this invention. These salts are easily converted again into the free form by the action of an acid or in vivo. Thus, the pharmacological effect of the camptothecin derivatives is not influenced by such treatments. A preferable salt of the camptothecin derivatives is the sodium or potassium salt.

In accordance with the present invention, there is also provided a process for the preparation of the camptothecin derivatives. In one embodiment of the process, camptothecin derivatives of the general formula:

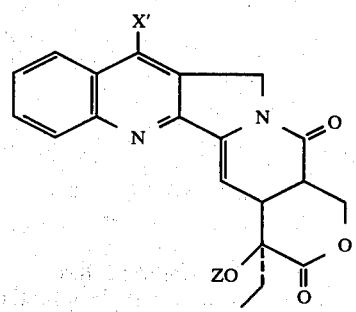

[I']

wherein X' is the grouping $COOR^4$ or $CH_2OR$ where $R^4$ is H or a lower alkyl group and R is H, an alkyl group or an acyl group, and Z is H or an acyl group, as well as water-soluble alkali metal salts thereof, are prepared by subjecting camptothecin to a radical reaction with a hydroxymethyl compound of the general formula:

$$A—CH_2OH \quad [II]$$

wherein A is H, COOH or $CH_2OH$, by the aid of sulfuric acid and peroxide in an aqueous medium and then optionally treating the resultant 7-hydroxymethylcamptothecin with an alkylating agent or an acylating agent to convert the 7-hydroxymethyl group into a 7-alkoxymethyl group or into a 7-acyloxymethyl group with or without simultaneous acylation of the 20-hydroxy group, or optionally oxidizing the resultant 7-hydroxymethylcamptothecin to 7-carboxycamptothecin and then optionally esterifying the 7-carboxy group with a lower alkanol to form a 7-alkoxycarbonyl group, and if desired, converting the free compound into an alkali metal salt thereof or vice versa.

Camptothecin used as the starting material may be any of the natural and synthetically obtained forms, i.e. the d-, l- and dl-forms.

The hydroxymethyl compounds of the general formula [II] are easily commercially available among which methanol, i.e. the case of A being H, is preferable.

In the first main step, the radical reaction is normally carried out in an aqueous medium in the presence or absence of a transition metal ion. Accordingly, the operation for the first main step is carried out in principle by dissolving camptothecin in an aqueous solution of sulfuric acid and a hydroxymethyl compound such as methanol, adding a peroxide and maintaining the mixture under proper reaction conditions until the radical reaction is finished. Any of the peroxides known as radical reaction initiators can be used as the peroxide in this reaction. Preferable examples of the peroxides include inorganic peroxides such as hydrogen peroxide, persulfuric acid and salts thereof, for example, potassium persulfate, sodium persulfate, ammonium persulfate, barium peroxide, sodium peroxide, Caro's acid and salts thereof, and calcium peroxide, and organic peroxides such as tert-butyl hydroperoxide, benzoyl peroxide, lauroyl peroxide, caprylyl peroxide, DTBP (di-tert-butyl peroxide) and AIBN (2,2'-azobis-isobutyronitrile). Among these organic and inorganic peroxides, the use of hydrogen peroxide, a persulfate such as ammonium peroxide and tert-butyl hydroperoxide is preferable in the present invention.

The transition metal ion, if it is allowed to be present in the reaction medium, is supplied to the reaction medium from the corresponding salt which is capable of dissociating the ion in the reaction medium. Examples of such transition metal salt include silver salts such as silver nitrate, silver sulfate, silver carbonate and silver acetate, iron salts and oxides such as ferrous sulfate, ferrous chloride and iron monoxide, copper salts such as cuprous chloride, cupric sulfate, and cupric nitrate, cobalt salt such as cobalt acetate, cobalt sulfate, cobalt nitrate and cobalt acetate, nickel salts such as nickel nitrate, nickel sulfate and nickel chloride, lead salts such as lead acetate, mercury salts such as mercurous chloride and mercuric chloride, and cadmium compounds such as cadmium nitrate and cadmium chloride. Besides these compounds, thallium and zinc compounds such as zinc sulfate can also be used. The use of silver and iron compounds is most preferable. The transition metal ion may not be present in the reaction medium but the existence of the ion is recommended to promote the radical reaction quickly and efficiently. The transition metal salt is used within the range from an almost equimolar amount to an about 30 molar amount to camptothecin, preferably in a 10–30 molar amount. If the amount of the transition metal salt becomes smaller than the equimolar amount to camptothecin, the effect of promoting the radical reaction will hardly be recognized. On the other hand, no additional technical merits can be achieved by increasing the amount of the transition metal salt over a 30 molar proportion to camptothecin. The use of an excessively large amount of the transition metal salt will rather bring about undesirable effects in separation of the resulting product from the reaction mixture. The reaction conditions are represented by temperature and time. The reaction temperature varies widely from room temperature to the boiling point of the reaction mixture. The reaction time is usually within several hours to one day and generally depends on the reaction temperature adopted. If the transition metal ion is allowed to exist in the aqueous solution of sulfuric acid and methanol containing camptothecin and a peroxide is gradually added to the solution, the reaction is promoted at room temperature or in a warmed state to form 7-hydroxymethylcamptothecin in a higher yield.

A general operation for performing the first main step comprises dissolving camptothecin in an aqueous solution of sulfuric acid and the hydroxymethyl compound, adding the radical reaction initiator to the aqueous solution, maintaining the mixture at a temperature within the range from room temperature to the boiling point of the reaction mixture for several hours to one day and pouring the reaction mixture into ice water to separate the resultant 7-hydroxymethylcamptothecin as a precipitate from the reaction mixture. The precipitated crude crystals are collected by filtration or extraction of the reaction mixture with a water-immiscible organic solvent such as methylene chloride, chloroform, ethyl acetate, butyl alcohol, amyl alcohol, carbon tetrachloride and carbon disulfide. The use of chloroform is preferable for this purpose. The resultant crude 7-hydroxymethylcamptothecin can be purified according to a usual manner, for example, by recrystallization from dimethylformamide-dioxane, by thin layer chromatography, by high performance liquid chromatography or by a combination of these purification treatments.

7-Hydroxymethylcamptothecin thus prepared possesses excellent pharmacological properties and can be used directly as a medicament or is useful as an intermediate for preparing various camptothecin derivatives functionally substituted at the hydroxymethyl group in the 7-position thereof.

7-Hydroxymethylcamptothecin and 7-substituted camptothecins derived therefrom can be converted, if desired, into water-soluble alkali metal salts by treating the camptothecin derivative in free form with an alkali metal hydroxide or carbonate at room temperature or at an elevated temperature. This alkali metal salt is formed by opening of the lactone ring (ring E). However, such alkali metal salt can easily be converted into the free form by treating the salt with an acid whereby the lactone ring is formed with simultaneous dehydration (dehydrocyclization). Camptothecin and its derivatives do not form in principle acid-addition salts, though they contain two tertiary nitrogen atoms.

The hydroxymethyl group of 7-hydroxymethylcamptothecin can optionally be treated with an alkylating agent to prepare the corresponding 7-alkoxymethyl derivatives or with an acylating agent to prepare the corresponding 7-acyloxymethylcamptothecin or with an oxidizing agent to prepare the corresponding 7-carboxycamptothecin which may further be converted with a hydroxy compound such as an alcohol into an ester of camptothecin-7-carboxylic acid.

The alkylation of 7-hydroxymethylcamptothecin is carried out according to a method known per se, for example, by reacting 7-hydroxymethylcamptothecin with an alkanol corresponding to the alkyl moiety of 7-alkoxymethylcamptothecin to be prepared. The above reaction is usually carried out by heating the reaction mixture in the presence of an acid catalyst such as hydrochloric acid, sulfuric acid, fluoroboric acid, benzenesulfuric acid, p-toluenesulfonic acid and borontrifluoride etherate. Illustrative of the alkanol as alkylating agent are, for example, methanol, ethanol, propanol, butanol, hexanol, deanol and hexadecanol. The use of a lower alkanol such as methanol or ethanol is preferable. The operation for this O-alkylation is performed normally by dissolving 7-hydroxymethylcamptothecin in the alkylating agent, for example, ethanol, adding to the solution any of the acid catalysts above mentioned and heating the mixture. The resulting 7-alkoxymethylcamptothecin can be separated from the reaction mixture by extraction with an organic solvent and purified according to a method known per se, for example, by column, thin layer, or high performance liquid chromatographic techniques or a combination of these chromatographic techniques.

The acylation of 7-hydroxymethylcamptothecin is carried out according to a method known per se by reacting 7-hydroxymethylcamptothecin with an acylating agent normally in the presence of a dehydration agent or an acid-binding agent. Illustrative of the acylating agent are carboxylic acids and reactive functional derivatives thereof as well as sulfonic acids and reactive functional derivatives thereof and alkyl hemisulfates, such as formic acid, acetic acid, propionic acid, butyric acid, phenylacetic acid, succinic acid, trifluoroacetic acid and the like aliphatic carboxylic acids, benzoic acid and its nucleus-substituted derivatives, naphthoic acid and the like aromatic acids, alkanesulfonic acids, for example, methanesulfonic acid and ethanesulfonic acid, arylsulfonic acids, for example, benzenesulfonic acid, and p-toluenesulfonic acid, and lauryl hemisulfate, and halides or lower alkyl esters of these acids, for example, acetyl chloride and propionyl bromide. Preferable examples of the acid-binding agent include inorganic bases such as sodium carbonate, potassium bicarbonate, caustic alkali and calcium carbonate, and organic bases such as triethylamine, pyridine and tetramethylammonium hydroxide. In general, the use of a reactive functional derivative of the carboxylic or sulfonic acid is preferable. In case the acylating agent is a carboxylic acid, an acid anhydride, e.g. acetic anhydride is preferably used as the reactive functional derivative of the carboxylic acid. The reaction is promoted in the presence of the acid-binding agent at room temperature or at an elevated temperature.

Since 7-hydroxymethylcamptothecin has two hydroxy groups, either of 7-acyloxymethylcamptothecins and 7-acyloxy-20-O-acyl-camptothecins are prepared predominantly by properly controlling the proportion of the acylating agent to camptothecin and the reaction temperature. When a large excess of the acylating agent is used or a higher reaction temperature is employed, the two hydroxy groups (one of them is a primary hydroxy group in the hydroxymethyl group and the other is a tertiary hydroxy group bound to the 20-position) tend to undergo acylation, thus resulting in the formation of the diacylated product in a larger proportion. Contrary to this, when an almost or slightly excess stoichiometrical amount of the acylating agent is used for the starting 7-hydroxymethyl camptothecin or the reaction is carried out at a lower temperature, for example, at room temperature, the hydroxy group in the 7-hydroxymethyl group alone tends to undergo acylation. Accordingly, if 7-acyloxymethylcamptothecin are to be prepared predominantly, it is desirable to use the acylating agent in an almost equimolar amount with respect to the starting 7-hydroxymethylcamptothecin and to conduct the reaction at a temperature as low as possible. On the other hand, if the diacylated product is to be prepared, the acylating agent should be used in large excess (at least two molar proportion) and the reaction should be conducted at a higher temperature.

In case a diacylated product wherein the acyl group in the 7-acyloxymethyl group is different from that in the 20-position is to be prepared, the acylation of the 7-hydroxymethyl group with an acylating agent is first carried out carefully under the above mentioned condition and then the O-acylation of the hydroxy group in the 20-position is carried out with a different acylating agent.

The acylating reaction is normally performed according to a conventional method by dissolving 7-hydroxymethylcamptothecin in an inert solvent containing a dehydrating agent or an acid-binding agent and adding an acylating agent while stirring the mixture at room temperature or at an elevated temperature. The reaction can be promoted by using a conventional esterifying catalyst such as sulfuric acid, sodium acetate, pyridine, fluoroboric acid, p-toluenesulfonic acid and strongly acidic ion-exchangers such as Amberlite IR-100, IR-105, IR-112 and IR-120 (Rohm & Haas Co., U.S.A.), Dowex 50-X1, X2 and Dowex 30 (Dow Chemical Co., U.S.A.) and Dia-ion SK #1, K and RK (Mitsubishi Kasei Co., Japan).

7-Hydroxymethylcamptothecin obtained in the first main step can be oxidized in the successive step with an oxidizer capable of converting the hydroxymethyl group into a carboxy group according to a method known per se. Such oxidizer is well known and is selected, for example, from anhydrous chromates, bichromates and permanganates. This oxidation reaction is usually carried out at room temperature or an elevated temperature in the presence of acetone, acetic acid, sulfuric acid or the like as the reaction medium whereby 7-carboxycamptothecin (or camptothecin-7-carboxylic acid) is obtained. This carboxylic acid can be purified, if necessary, by recrystallization from dioxane.

7-Carboxycamptothecin thus obtained may further be converted according to a conventional esterification method into 7-alkoxycarbonylcamptothecin. This esterification reaction is carried out in a usual manner by dissolving or suspending 7carboxylcamptothecin in an excess amount of a lower alkanol preferably with 1–8 carbon atoms, adding an esterifying catalyst and heating the mixture. Any of the esterifying catalysts referred to in the acylation of a 7-hydroxymethyl group is suited for this purpose. Alternatively, a mixture of 7-carboxycamptothecin, an at least equimolar amount of a lower alkanol and an esterifying catalyst in benzene to toluene is refluxed while removing only water formed during the reaction and distilled as an azeotrope with the solvents by means of an appropriate water-separator. Illustrative of the lower alkanol are, for example, methanol, ethanol, n-propanol, isopropanol, n-butanol, tert-butanol, hexanol, heptanol and octanol. Preferable examples of the esterifying catalyst are well known in the art and include sulfuric acid, hydrochloric acid, p-toluenesulfonic acid and borontrifluoride etherate. The resulting ester can be purified by recrystallization, for example, from ethanol-dioxane.

According to a variant of the first main step of this embodiment, camptothecin derivatives of the general formula:

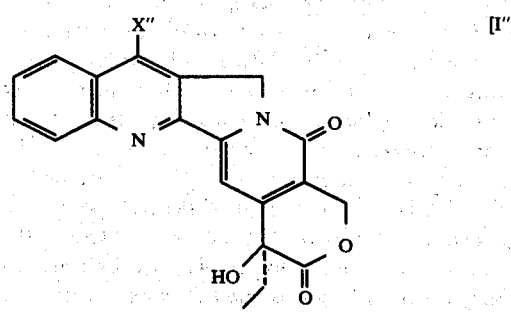

[I'']

wherein X" is an alkyl group or an aralkyl group, are prepared by subjecting camptothecin to a radical reaction with an organic compound of the general formula:

X"—Q [II']

wherein Q is the grouping —CH$_2$OH, —COOH, —CHO, —COX" or

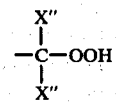

and X" has the same meaning as given above, by the aid of sulfuric acid and a peroxide in an aqueous medium in the presence of a transition metal ion.

When Q is —CH$_2$OH, the organic compound of the general formula [II'] is an alkanol or an aralkanol. Preferable examples of such alkanol or aralkanol include straight or branched chain primary alcohols such as ethanol, propanol, butanol, pentanol, hexanol, octanol, 3-methylpentanol, isoamyl alcohol, cyclohexylmethanol, cyclopentylmethanol, decanol, phenethyl alcohol and phenylpropanol. When Q is —COOH, the organic compound is a fatty acid or an arylfatty acids. Illustrative of such acid are, for example, acetic acid, propionic acid, butyric acid, hexanoic acid, octanoic acid, phenylacetic acid, β-phenylpropionic acid. When Q is —CHO, the organic compound is an aldehyde such as acetaldehyde, propionaldehyde, butyraldehyde, caprylyldehyde or phenylacetaldehyde. When Q is —COX", the organic compound is a dialkyl ether or a diaralkyl ether. In this case, the two alkyl moieties of the dialkyl ether may be the same or different. Similarly, when Q is

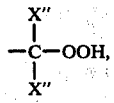

the organic compound is for example, a tert-alkyl hydroperoxide in which the three alkyl groups may be the same or different. A preferable compound of this type is tert-butyl hydroperoxide.

This radical reaction is carried out in principle by dissolving in water a transition metal salt capable of dissociating the transition metal ion, camptothecin, sulfuric acid and a compound of the general formula [II'] in any order of succession and adding a peroxide and stirring the mixture. Usually, a compound of the general formula [II'] and a transition metal salt are dissolved in water and then camptothecin and sulfuric acid are added in the noted order to the solution. A peroxide is added to the solution under agitation and ice cooling and the agitation is continued even after the temperature is raised to room temperature. After completion of the reaction, ice water is added to the reaction mixture and the resulting product is extracted with a water-immiscible organic solvent such as chloroform and purified, for example, by column chromatography followed by recrystallization from an organic solvent such as n-hexane-chloroform.

Preferable examples of the transition metal salt capable of dissociating the transition metal ion in the reaction medium include silver salts such as silver nitrate, silver sulfate, silver carbonate and silver acetate, iron salts and oxides such as ferrous sulfate, ferrous chloride and iron monoxide, copper salts such as cuprous chloride, cupric sulfate, cupric nitrate, cobalt salts such as cobalt chloride, cobalt sulfate, cobalt nitrate and cobalt acetate, nickel salts such as nickel nitrate, nickel sulfate and nickel bromide. Besides these compounds, salts of lead, mercury, cadmium thallium and zinc, such as lead acetate, mercurous chloride, cadmium nitrate and zinc sulfate, can also be used equivalently. Examples of the peroxide include inorganic peroxides such as hydrogen peroxide, persulfates such as potassium persulfate, sodium persulfate, Caro's acid and its salts, barium peroxide, calcium peroxide, sodium peroxide and organic peroxides such as tert-butyl hydroperoxide, benzoyl peroxide, lauroyl peroxide, caprylyl peroxide, DTBP and AIBN.

In case a higher alcohol or the like compound which is sparingly soluble in water is used as a compound of the general formula [II'], a dissolution assistant is used to promote dissolution of such sparingly soluble compound in water. Utilizable as the dissolution assistant are polar organic solvents which are inert to the reaction and capable of forming a homogeneous phase, such as acetic acid, dimethylformamide, acetonitrile, dioxane, dimethoxyethane and tetrahydrofuran. Various surfactants capable of forming a homogeneous phase, particularly nonionic surfactants may also be used for this purpose in place of the dissolution assistant.

The compound of the general formula [II'] is preferably used in a large excess in molar ratio to camptothecin. For example, about 20 molar proportion of the compound is used for camptothecin. The transition metal salt and the peroxide are used respectively in excess, for example, about 5-8 molar excess to the amount of camptothecin used. The reason why the compound of the general formula [II'] is used in large excess is that an excessively sufficient amount of a radical species allowed to be present in the reaction medium serves not only to prevent occurrence of any side reaction which affords by-products but also to promote the formation of the end product normally within a reasonable period of time.

In the above radical reaction, it is of interest that when a straight or branched chain primary alcohol such as ethanol or isobutanol is used as the compound of the general formula [II'], the moiety of X'', e.g. methyl group in the case of using ethanol or isopropyl group in the case of using isobutanol (i.e. the moiety of the primary alcohol excluding the terminal grouping —CH$_2$OH) is introduced into the 7-position of camptothecin. In other words, an alkyl moiety of the alcohol from which one carbon atom has been excluded is introduced in all cases into the 7-position of camptothecin. When a cycloalkylmethanol such as cyclohexylmethanol or cyclopentylmethanol is used as the organic compound X''—Q, the cycloalkyl group can directly be introduced into the 7-position of camptothecin. In a similar manner, an aralkyl group such as a benzyl group can be introduced by using an aralkanol composed of the aralkyl moiety and the grouping CH$_2$OH, e.g. phenethyl alcohol as the organic compound X''—Q. When a fatty acid or an arylfatty acid is used as the organic compound X''—Q, the moiety of the carboxylic acid from which the grouping —COOH has been eliminated is introduced into the 7-position of camptothecin. For example, when acetic acid or isovaleric acid is used as the organic compound, a methyl group or isobutyl group is introduced into the 7-position of camptothecin, respectively. Accordingly, the use of phenylacetic acid serves to introduce a benzyl group into camptothecin. The same applies to the case wherein an aldehyde of X''—CHO is used as the organic compound. In this case, the moiety of such aldehyde from which the grouping CHO has been removed is introduced into the 7-position of camptothecin. Thus, the use of acetaldehyde or propionaldehyde affords 7-methyl- or 7-ethylcamptothecin, respectively. When a ketone X''—CO—X'' (Q=COX'') in which two alkyl and/or aralkyl moieties (X'') may be the same or different is used as the organic compound X''—Q, either of the moieties (X'') is introduced into the 7-position of camptothecin. If a symmetrical ketone such as acetone or diethyl ketone is used, a methyl group or ethyl group is introduced. If, however, an asymmetrical ketone such as methyl ethyl ketone or methyl isobutyl ketone is used as the organic compound, a mixture of a methyl group and ethyl group or a mixture of a methyl group and isobutyl group is introduced into the 7-position of camptothecin. In case the organic compound X''—Q is a hydroperoxide, Q is the grouping

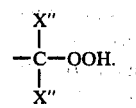

In case tert-butyl hydroperoxide is used as the organic compound X''—Q, the three alkyl moiety (X'') is the same and a methyl group is introduced into the 7-position of camptothecin. However, when one or two alkyl moieties (X'') in Q are different, a mixture of two or three different kinds of alkyl group is introduced into the 7-position of camptothecin. Thus, care should be taken when the organic compound X''—Q is a ketone or hydroperoxide.

7-Alkylcamptothecins obtained in any of the above mentioned variant of the first step can optionally be treated with an oxidizing agent to form the corresponding 7-carboxycamptothecin (camptothecin-7-carboxylic acid) which may further be esterified, if desired, with a lower alkanol to form an ester thereof (a lower alkyl camptothecin-7-carboxylate).

Any of the oxidizers capable of oxidizing an alkyl group such as a methyl group bound to an aromatic ring to a carboxyl group can be used for this optional oxidation treatment. Such oxidizer is well known in this art and is usually selected, for example, from anhydrous chromates, bichromates and permanganates.

This oxidation reaction is usually carried out at room temperature or at an elevated temperature in the presence of acetone, acetic acid, sulfuric acid or the like reaction medium. 7-Carboxycamptothecin thus obtained can be purified, if necessary, by recrystallization from dioxane. This product (7-carboxycamptothecin) may further be converted, if desired, according to a conventional esterification method [as described in the case of obtaining a lower alkyl camptothecin-7-carboxylate from 7-hydroxymethylcamptothecin via 7-carboxycamptothecin (camptothecin-7-carboxylic acid) in the optional after-treatment in this embodiment] into an ester of camptothecin-7-carboxylate.

According to another embodiment of the process of the present invention, camptothecin derivatives of the general formula:

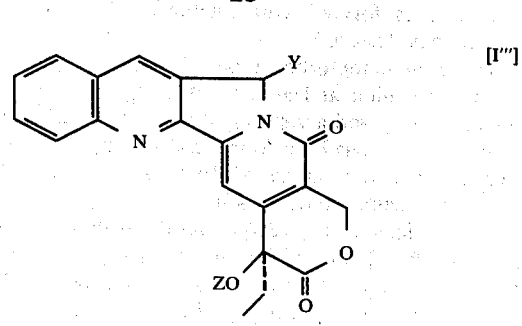

[I''']

wherein Y' is OH or the grouping $OR^3$ where $R^3$ is a lower alkyl group or an acyl group and Z is H or an acyl group, as well as water-soluble alkali metal salts are prepared by treating camptothecin with sulfuric acid and a persulfate in an aqueous medium containing a transition metal ion, and thereafter optionally treating the resultant 5-hydroxycamptothecin with an alkylating agent or an acylating agent to convert the hydroxy group in the 5-position into a 5-alkoxy group or into a 5-acyloxy group with or without simultaneous acylation of the hydroxy group in the 20-position.

In the first main step, the radical reaction is in principle carried out by dissolving camptothecin in a mixture of sulfuric acid and water, adding a transition metal salt and an aqueous solution of a persulfate to the solution and stirring the mixture while heating. Preferable examples of the transition metal salt capable of dissociating the transition metal ion in the reaction medium include silver salts such as silver nitrate, silver sulfate, silver carbonate and silver acetate, iron salts and oxides such as ferrous sulfate, ferrous chloride and iron monoxide, copper salts such as cuprous chloride, cupric sulfate and cupric nitrate, cobalt salts such as cobalt chloride, cobalt sulfate, cobalt nitrate and cobalt acetate, nickel salts such as nickel sulfate and nickel nitrate. Salts of lead, mercury, thallium, cadmium and zinc such as lead acetate, mercuric chloride, cadmium nitrate and zinc sulfate can also be used equivalently. Preferable are silver salts and iron compounds as mentioned above.

Illustrative of the persulfate are, for example, sodium persulfate, potassium persulfate, ammonium persulfate, and Caro's acid and its salts. In addition to these persulfates, any of the peroxides which are capable of forming a persulfate in the reaction medium containing sulfuric acid can also be used equivalently to the inherent persulfate. Preferable examples of such persulfate-forming peroxide are, for example, hydrogen peroxide, barium peroxide, calcium peroxide, sodium peroxide and organic peroxides such as tert-butyl hydroperoxide, benzoyl peroxide, lauroyl peroxide, caprylyl peroxide, DTBP and AIBN. The persulfate or a peroxide capable of forming a persulfate is used in an amount within the range of 5–30 molar proportion with respect to camptothecin. The mixing ratio of sulfuric acid to water is within the range from 10:90 to 90:10, with the ratio of 50:50 being preferable. No critical limitation exists in the proportion of camptothecin to sulfuric acid, but sulfuric acid is usually used in a large excess. The transition metal salt is normally used in an equimolar amount with respect to the amount of camptothecin used, but the salt may be used in excess. The reaction mixture can be heated up to the boiling temperature thereof and the reaction is usually finished within several hours after addition of the persulfate.

The radical reaction may be effected in the presence of acetic acid, bromoacetic acid, glycolic acid, dimethylformamide or the like polar solvent whereby the reaction time can be shortened and the yield of the product can be increased.

Diastereomers of 5-hydroxycamptothecin exist in connection with the configuration of the hydroxy group in the 5-position thereof. The two diastereomers can be separated by converting 5-hydroxycamptothecin into 5-acetoxycamptothecin and subjecting the latter to chromatography with silica gel. More precisely, 5-acetoxycamptothecin (a mixture of the two diastereomers) is subjected to thin layer chromatography with 1% methanol-chloroform as developing solvent whereby the 5-acetoxycamptothecin can be separated into the individual isomers having Rf values of 0.20 and 0.15. According to the NMR spectrograph of the two isomers, the methine proton in the 5-position and the methyl moiety of the acetoxy group in the 5-position of both isomers are observed at $\delta$ 7.96; 2.192 ppm and $\delta$ 7.91; 2.195 ppm, respectively. However, no substantial difference is observed between both isomers in peaks based on other hydrogens. In an NMR spectrograph of 5-hydroxycamptothecin prepared in the first main step, the methine proton in the 5-position is observed as two singlet peaks at $\delta$ 6.66 and $\delta$ 6.72 ppm each by 0.5 H. Thus, it is confirmed that 5-hydroxycamptothecin is a mixture (about 1:1) of the two diastereomers.

The new 5-hydroxycamptothecin thus prepared possesses excellent pharmacological properties and can be used directly as a medicament or is useful as an intermediate product for preparing various camptothecin derivatives functionally substituted at the hydroxy group in the 5-position thereof.

The hydroxy group in the 5-position of the 5-hydroxycamptothecin can optionally be treated with an alkylating agent to prepare the corresponding 5-alkoxycamptothecin derivatives or with an acylating agent to prepare the corresponding 5-acyloxycamptothecin derivatives.

The alkylation of 5-hydroxycamptothecin is conducted according to a method known per se, for example, by reacting 5-hydroxycamptothecin with a lower alkanol corresponding to the alkyl moiety $R^3$ of 5-alkoxycamptothecin to be prepared. The above reaction is usually carried out by heating the reaction mixture in the presence of an acid catalyst such as hydrochloric acid, sulfuric acid, fluoroboric acid, benzenesulfonic acid, p-toluenesulfonic acid and boron trifluoride etherate. Illustrative of the lower alkanol as alkylating agent are, for example, methanol, ethanol, n-propanol, isopropanol, n-butanol, isobutanol, tert-butanol, n-pentanol, n-hexanol, heptanol and octanol. The use of methanol or ethanol is preferable in ease of availability and handling. The operation for this O-alkylation is performed normally by dissolving 5-hydroxycamptothecin in an excess amount of the alkylating agent, for example, ethanol, adding to the solution any of the above mentioned catalysts and heating the mixture. The resulting 5-alkoxycamptothecin can be separated from the reaction mixture by extraction with an organic solvent and purified according to a method known per se, for example, by column or thin layer chromatography through silica gel.

The acylation of 5-hydroxycamptothecin is carried out according to a method known per se by reacting 5-hydroxycamptothecin with an acylating agent preferably in the form of a reaction derivative of an acid, if necessary, in the presence of an acid-binding agent.

Examples of the acylating agent include carboxylic acids and reactive functional derivatives thereof as well as sulfonic acids and reactive functional derivatives thereof and alkyl hemisulfates. Illustrative of such acylating agent are formic acid, acetic acid, propionic acid, butyric acid, phenylacetic acid, succinic acid, trifluoroacetic acid, and the like aliphatic carboxylic acids, benzoic acid and its nucleus-substituted derivatives, naphthoic acid and the like aromatic acids, alkanesulfonic acids, for example, methanesulfonic acid and ethanesulfonic acid, arylsulfonic acids, for example, benzenesulfonic acid and p-toluenesulfonic acid, and lauryl hemisulfate, and halides or lower alkyl esters of these acids, for example, acetyl chloride and propionyl bromide. In case the acylating agent is a carboxylic acid, an acid anhydride is preferably used as a reactive functional derivative of the carboxylic acid. Preferable examples of the acid-binding agent which is used to promote the reaction between 5-hydroxycamptothecin and the acylating agent in the form of a reactive functional derivative of an acid include inorganic bases such as sodium carbonate, potassium bicarbonate, caustic alkali and calcium carbonate, and organic bases such as triethylamine, pyridine, picoline, lutidine, collidine and tetramethylammonium hydroxide. In general, the use of a reactive functional derivative of the carboxylic or sulfonic acid is preferable and the reaction is promoted in the presence of the acid-binding agent at room temperature or at an elevated temperature.

Since 5-hydroxycamptothecin has two hydroxy groups, either of 5-acyloxycamptothecins and 5-acyloxy-20-O-acyl-camptothecins are prepared mainly by properly controlling the proportion of the acylating agent and the reaction temperature. When a large excess of the acylating agent is used or a higher reaction temperature is employed, the two hydroxy groups tend to undergo acylation, thus resulting in the formation of the diacylated product in a larger proportion. Contrary to this, when an almost or slightly excess stoichiometrical amount of the acylating agent is used for the 5-hydroxycamptothecin or the reaction is carried out at a lower temperature, for example, at room temperature, the hydroxy group in the 5-position alone tends to undergo acylation. Accordingly, if 5-acyloxycamptothecins are to be prepared chiefly, it is desired to use the acylating agent in an almost equimolar amount with respect to the 5-hydroxycamptothecin and to conduct the reaction at a temperature as low as possible. On the other hand, if the diacylated product is to be prepared, the acylating agent must be used in large excess (at least two molar proportion) and the reaction should be conducted at a higher temperature.

Although two diastereomers (R- and S-isomers) of 5-hydroxycamtothecin exist in connection with the configuration of the hydroxy group in the 5-position thereof, they can be separated by converting the 5-hydroxy compound into the 5-acetoxy compound and subjecting the latter to thin layer chromatography in a manner as described above.

5-Hydroxycamptothecin and 5-substituted camptothecins derived therefrom can be converted, if desired, into water-soluble alkali metal salts by treating the camptothecin derivative in free form with an alkali metal hydroxide or carbonate at room temperature or at an elevated temperature. This alkali metal salt is formed by opening of the lactone ring (ring E). However, such alkali metal salt can easily be converted into the free form by treating the salt with an acid whereby the lactone ring is formed with simultaneous dehydration (dehydroxyclization).

The new camptothecin derivatives of the present invention exhibit at least one of a high level of anti-tumor activity and a very slight toxicity. As a result of animal tests, it has been found that the majority of the camptothecin derivatives of the present invention are superior to camptothecin itself in anti-tumor activity to lymphatic leukemia L-1210 (from the National Cancer Institute strain). The toxicity of the new camptothecin derivatives of the present invention is generally low. The pharmacological activity of the new camptothecin derivatives of the present invention is as high as 100–380% in terms of T/C % (median life-span of treated mice divided by median life-span of untreated control mice in percentage—one of the standard methods for evaluating anti-tumor activity) in comparison with camptothecin itself. Thus, the new camptothecin derivatives of the present invention are useful as anti-tumor agents or as intermediate products for preparing other useful derivatives.

The present invention will now be illustrated in more detail by way of examples. In these examples, the relation between part and percentage is by weight unless otherwise indicated.

All melting points were measured in a capillary tube and were uncorrected. NMR spectra were obtained by Hitachi R-22 90MC and JEOL FX-100 NMR spectrophotometer, using TMS as an internal reference. Mass spectra were recorded on a Hitachi RMS-4 or a JEOL JMS D300 instrument. The IR and UV spectra were measured on a JASCO IRA-1 or on a Hitachi EPS-3 spectrophotometer, respectively. Optical rotation was measured on a Yanagimoto Yanaco OR-50 automatic polarimeter.

EXAMPLE 1

(Preparation of 7-hydroxymethylcamptothecin)

Camptothecin (100 mg, 0.287 m-mol) was suspended in methanol (25 ml) and then dissolved therein by addition under ice-cooling of 75% sulfuric acid (10 ml). To the solution was added dropwise under reflux with stirring an aqueous solution (100 ml) of ammonium persulfate (15 g, 0.0657 mol) over 16 hours. The reaction mixture was poured into ice water (100 ml) and the organic matter was extracted with a mixture (1:1, 500 ml) of dioxane-chloroform and then thrice with chloroform (100 ml×3). The organic phases were combined, dried with anhydrous magnesium sulfate, filtered and then evaporated until dryness under reduced pressure. The remaining solid having an orange color was warmed (50°–60° C.) with methanol (200 ml) and stirred for 30 minutes. An insoluble matter was collected by filtration, dried under reduced pressure and recrystallized from dimethylformamide-dioxane whereupon 40 mg (36.9%) of 7-hydroxymethylcamptothecin were obtained as light yellow white prismatic crystals having a melting point of 274°–276° C. (dec.). Rf value 0.125 (5% methanol-chloroform).

IR$\nu_{max}^{KBr}$ cm$^{-1}$: 3300, 2960, 1770, 1665, 1605, 1470, 1200, 1170, 1115, 770.

NMR (DMSO-d$_6$) δ ppm: 0.90(3H, t, J=7 Hz), 1.88(2H, q, J=7 Hz), 5.23(2H, s) 5.34(2H, s), 5.40(2H, s), 7.30(1H, s), 7.55–8.13(4H, m).

MS m/e: 378.1283 [M$^+$] (C$_{21}$H$_{18}$N$_2$O$_5$=378.1209).

UV $\lambda_{max}^{EtOH}$nm: 220, 245, 253.5, 292, 302, 335(sh), 359, 372.

EXAMPLE 2

(Preparation of 7-hydroxymethylcamptothecin)

Camptothecin (3.00 g, 8.61 m-mol) was suspended in methanol (90 ml) and then dissolved therein by addition of 75% sulfuric acid (75 ml) and 75 ml of water. To the solution was added $FeSO_4 \cdot 7H_2O$ (40 g, 0.143 mol) and then was added dropwise under ice-cooling and agitation 30% hydrogen peroxide (15 ml) over 2 hours. After addition of the hydrogen peroxide, the reaction mixture was stirred for 14 hours at room temperature and poured into ice water (1 l). The yellowish brown solid precipitated was collected by filtration and dried under reduced pressure whereby 2.5 g of 7-hydroxymethylcamptothecin were obtained. The filtrate was extracted with chloroform (250 ml×4) thereby obtaining 200 mg of crude crystals of the product. 2.7 Grams (82.9%) in toto of 7-hydroxymethylcamptothecin were obtained, which was identified to be the same product as obtained in Example 1 by way of IR-absorption spectra and thin layer chromatography.

EXAMPLE 3

(Preparation of 7-hydroxymethylcamptothecin)

Camptothecin (50 mg, 0.143 m-mol) was dissolved in 75% sulfuric acid (3 ml). To this solution were added glycolic acid (500 mg, 6.57 m-mol) and silver nitrate (250 mg, 1.31 m-mol) and then was added dropwise under heating (100°–110° C.) and agitation and aqueous solution (15 ml) of ammonium persulfate (3.00 g, 0.0131 m-mol) over 2 hours. After the reaction mixture was allowed to cool, ice water (100 ml) was poured into the reaction mixture which was then extracted with chloroform (100 ml×3). The chloroform layers were combined, washed with a 7% aqueous solution of sodium bicarbonate (300 ml) and then with a saturated edible salt solution (100 ml), dried with anhydrous magnesium sulfate, filtered and evaporated until dryness under reduced pressure. The residue was subjected to thin layer chromatography (5% methanol-chloroform) to effect separation and purification of 7-hydroxymethylcamptothecin whereupon 10.3 mg (19.0%) of pure 7-hydroxymethylcamptothecin were obtained. Besides this, 10.7 mg of camptothecin were recovered.

EXAMPLE 4

(Preparation of 5-hydroxycamptothecin)

Camptothecin (100 mg, 0.287 m-mol) was dissolved in 75% sulfuric acid (5 ml). To this solution was added silver nitrate (50 mg, 0.295 m-mol) and then was added dropwise under heating (100°–110° C.) and agitation an aqueous solution (20 ml) of ammonium persulfate (1.96 g, 8.59 m-mol) over 1.5 hours. The heating and agitation were continued for 3 hours. After the reaction mixture was allowed to cool, the reaction mixture was diluted with water to 300 ml and was then extracted with chloroform (100 ml×5). The chloroform layers were combined, dried with anhydrous magnesium sulfate, filtered and evaporated until dryness under reduced pressure. The residue was subjected to thin layer chromatography to effect separation and purification whereupon 10.5 mg of camptothecin were recovered and 5-hydroxycamptothecin was obtained as a light yellow white solid. The yield was 10.3 mg (10.8%).

$IR\nu_{max}^{KBr}$ cm$^{-1}$: 3340, 2960, 1750, 1660, 1600, 1235, 1165.

NMR (DMSO-d$_6$) δ ppm: 1.01(3H, t, J=7.5 Hz), 1.91(2H, q, J=7.5 Hz), 4.87(1H, br, D$_2$O ex.), 5.25, 5.52(two 1H s, dxd, J=17 Hz), 6.66(0.5H, s), 6.72(0.5H, s), 7.31(1H, br, s), 7.50–8.35(4H, m), 8.52(1H, br, s).

MS m/e: 364.1041 [M+] ($C_{20}H_{16}N_2O_5$=364.1053).

UV $\lambda_{max}^{EtOH}$ nm: 217, 224(sh), 248(sh), 257, 295, 336(sh), 357, 370(sh).

EXAMPLE 5

(Preparation of 5-hydroxycamptothecin)

Camptothecin (350 mg, 1 m-mol) was dissolved in concentrated sulfuric acid and bromoacetic acid (13.9 g) while warming. To this solution was added silver nitrate (170 mg, 1 m-mol) and then was added dropwise under heating (110°–120° C.) and agitation an aqueous solution (100 ml) of ammonium persulfate (7.0 g, 0.0307 mol) over about 3 hours. The heating and agitation were continued for one hour. After the reaction mixture was allowed to cool, the reaction mixture was diluted with water to 100 ml and was then extracted with chloroform-dioxane(500 ml–200 ml). The organic phase was washed with a 5% aqueous solution of sodium bicarbonate (500 ml), dried with anhydrous magnesium sulfate, filtered and evaporated until dryness under reduced pressure. The residue was purified by recrystallization from n-hexane-chloroform whereupon 5-hydroxycamptothecin was obtained as a light yellow white solid. The yield was 149 mg (39%). This product was identified to be the same as the sample obtained in Example 4 by way of IR-absorption spectra and thin layer chromatography.

EXAMPLE 6

(Preparation of 5-hydroxycamptothecin)

Camptothecin (1.30 g, 3.69 m-mol) was dissolved in 45% sulfuric acid (40 ml). To this solution were added bromoacetic acid (1.54 g), 0.011 mol) and ferrous sulfate heptahydrate (1.02 g, 3.69 m-mol) and then was added dropwise under heating (90°–100° C.) and agitation an aqueous solution (100 ml) of ammonium persulfate (3.80 g, 0.016 mol) in portions over 4.5 hours. The heating and agitation were continued for 3.5 hours. After the reaction mixture was allowed to cool, the reaction mixture was diluted with ice water to about one liter and was then extracted with chloroform (250 ml×6). The chloroform layers were combined, dried with anhydrous magnesium sulfate, filtered and evaporated until dryness under reduced pressure. The residue was recrystallized from n-hexane-chloroform whereupon 5-hydroxycamptothecin was obtained as a light yellow white solid. The yield was 656 mg (48.5%). This product was identical in IR-absorption spectra with the product obtained in the preceding Example.

EXAMPLE 7

(Preparation of 20-O-acetyl-7-acetoxymethylcamptothecin)

7-Hydroxymethylcamptothecin (30 mg, 0.0793 m-mol) was dissolved in acetic anhydride (1 ml). Pyridine (0.1 ml) was added to the solution and the mixture was heated (110°–120° C.) with stirring for 2 hours. The reaction mixture was evaporated until dryness under reduced pressure. Water (3 ml) was added to the residue and the precipitate was collected by filtration, thoroughly washed with water (5 ml) and dried under reduced pressure whereupon crude crystals of 20-O-acetyl-7-acetoxymethylcamptothecin were obtained. The yield was 35 mg (98.5%). Recrystallization of this crude product from ethyl alcohol for purification gave 25 mg (68.4%) of light yellow white needle crystals. M.P. 291°–293° C. (dec.).

IR$\nu_{max}^{KBr}$ cm$^{-1}$: 2980, 1750, 1670, 1610, 1240, 770.

NMR (CDCl$_3$) δ ppm: 0.99(3H, t, J=7.5 Hz), 2.24(2H, q, J=7.5 Hz), 2.19(3H, s), 2.23(3H, s), 5.47(2H, s), 5.57, 5.75(two 1H s, dxd, J=18 Hz), 5.77(2H, s), 7.26(1H, s), 7.63–8.46(4H, m).

MS m/e: 462.1401 [M+] for $C_{25}H_{22}N_2O_7$=462.1419.

EXAMPLE 8

(Preparation of 7-acetoxymethylcamptothecin)

7-Hydroxymethylcamptothecin (150 mg, 0.431 m-mol) was dissolved in a mixture of pyridine (20 ml) and dimethylformamide (2 ml). To this solution was added under agitation at room temperature acetic anhydride (105 mg, 1.03 m-mol) in small portions over 7 hours. The reaction mixture was evaporated until dryness under reduced pressure and the residue was taken up in chloroform (250 ml). The solution was shaken first with a 5% aqueous solution (100 ml) of sodium bicarbonate and then with 5% hydrochloric acid (100 ml). The chloroform layer obtained was washed with a saturated edible salt solution (100 ml), dried with anhydrous magnesium sulfate, filtered and evaporated until dryness under reduced pressure. The residue was purified by recrystallization from n-hexane-chloroform whereupon 142 mg (78.4%) of 7-acetoxymethylcamptothecin were obtained as light yellow white needle crystals. M.P. 277°–279° C. (dec.).

IR$\nu_{max}^{KBr}$ cm$^{-1}$: 3320, 2970, 1770, 1660, 1610, 1235, 770.

NMR (in CDCl$_3$) δ ppm: 1.03(3H, t, J=7 Hz), 1.89(2H, q, J=7 Hz), 2.18(3H, s), 5.44(2H, s), 5.26, 5.72(two 1H s, dxd, J=16.5 Hz), 5.71(2H, s), 7.70 (1H, s), 7.58–8.28 (4H, m).

MS m/e: 420.1369 [M+] for $C_{23}H_{20}N_2O_6$=420.1314.

UV$\lambda_{max}^{EtOH}$ nm: 220, 246(sh), 255, 292, 336(sh), 360, 373.

EXAMPLE 9

(Preparation of 7-succinoyloxymethylcamptothecin)

7-Hydroxymethylcamptothecin (200 mg, 0.529 m-mol) was dissolved in pyridine (30 ml). To this solution were added under heating (70°–80° C.) and agitation 100 mg of solid succinic anhydride as such. The heating and agitation were continued for 12 hours. The mixture was reacted together for 3 days under continuous heating and agitation while supplying additional succinic anhydride in an amount of 100 mg per day. Thus, 400 mg (4 m-mols) of succinic anhydride in all were used for the reaction. The resultant reaction mixture was evaporated until dryness under reduced pressure and the residue was taken up in ethanol and decolored with active carbon. The ethanol was evaporated until dryness under reduced pressure whereupon 235 mg (93%) of light yellow white prismatic crystals were obtained. This crude product was purified by recrystallization from n-hexane-ethanol whereupon 185 mg (73.2%) of 7-succinoyloxymethylcamptothecin were obtained as light yellow white prismatic crystals. M.P. 287–289 (dec.).

IR$\nu_{max}^{KBr}$ cm$^{-1}$: 3400–2750, 2960, 1750(vs), 1660, 1605, 1420, 1170, 775.

NMR (DMSO-d$_6$) δ ppm: 0.94(3H, t, J=7 Hz), 1.94(2H, q, J=7 Hz), 2.55(4H, br), 5.44(4H, brs), 5.80(2H, s), 7.40(1H, s), 7.65–8.43(4H, m).

EXAMPLE 10

(Preparation of 20-O-trifluoroacetyl-7-trifluoroacetoxymethylcamptothecin)

7-Hydroxymethylcamptothecin (200 mg, 0.529 m-mol) was dissolved in pyridine (40 ml) under warming. After allowing the solution to cool, trifluoroacetic anhydride (300 mg, 1.43 m-mol) was added and the mixture was stirred for 8 hours at 40° C. The reaction mixture was concentrated until dryness under reduced pressure and the residue was subjected to separation and purification by way of column chromatography (chloroform) through silica gel (50 g) whereby 20-O-trifluoroacetyl-7-trifluoroacetoxymethylcamptothecin was obtained as light yellow white crystals. The yield was 120 mg (39.7%).

IR$\nu_{max}^{KBr}$ cm$^{-1}$: 3340, 1760, 1660, 1600, 1235, 1160, 765.

M.P. 264°–267° C. (dec.).

EXAMPLE 11

(Preparation of 7-benzoyloxymethylcamptothecin)

7-Hydroxymethylcamptothecin (200 mg, 0.592 m-mol) was dissolved in pyridine (30 ml) under warming. Benzoyl chloride (260.2 mg, 1.85 m-mol) was added to this solution and the mixture was stirred for 15 hours at 50°–60° C. The pyridine was distilled off under reduced pressure and the residue was taken up in chloroform (30 ml). The solution was shaken first with a 5% aqueous solution (500 ml) of sodium hydrogen carbonate and then with 5% hydrochloric acid (500 ml). The chloroform layer was dried with anhydrous magnesium sulfate, filtered and evaporated until dryness under reduced pressure. The residue was purified by recrystallization from methanol whereupon 148 mg (57.9%) of 7-benzoyloxymethylcamptothecin were obtained as light yellow white needle crystals. M.P. 298° C.~(dec.).

IR$\nu_{max}^{KBr}$ cm$^{-1}$: 3420, 2940, 1770, 1730, 1675, 1610, 1460, 1280, 1110, 770, 715.

NMR (CDCl$_3$) δ ppm: 1.09(3H, t, J=7.5 Hz), 1.93(2H, q, J=7.5 Hz), 5.55(4H, br s), 5.92(2H, s), 7.47(1H, s), 7.54–8.30(9H, m).

MS m/e: 482 [M+] ($C_{28}H_{22}N_2O_6$=482).

EXAMPLE 12

(Preparation of 7-propionyloxymethylcamptothecin)

7-Hydroxymethylcamptothecin (378 mg, 1 m-mol) was dissolved in anhydrous dimethylformamide (80 ml) under warming. After cooling of the solution, anhydrous pyridine (1 ml) and propionic anhydride (1 ml, 8 eq.) were added and the mixture was stirred for 24 hours at room temperature. After completion of the reaction, ethanol (10 ml) was added to the mixture with stirring for a while to decompose the excess of the anhydride and the solvents were then distilled off under reduced pressure. The residue was purified by way of column chromatography through silica gel (10 g) whereby 420 mg (96.8%) of crude 7-propionyloxymethylcamptothecin crystals were obtained. Recrystallization of the crude product from n-hexane-chloroform gave 210 mg (48.4%) of light yellow white needle crystals. M.P. 279°–280° C.

IR$_{max}^{KBr}$ νcm$^{-1}$: 3230, 1740, 1655, 1595, 1460, 1165, 765.

NMR (in CDCl$_3$) δ ppm: 1.05(3H, t, J=7 Hz), 1.18(3H, t, J=7 Hz), 1.91(2H, q, J=7 Hz), 2.47(2H, q, J=7 Hz), 5.28(2H, d, J=17 Hz), 5.44(2H, s), 5.70 (2H, d, J=17 Hz), 5.71(2H, s), 7.63(1H, s) 7.70–8.30(4H, m).

MS: m/e 434 [M+] for C$_{24}$H$_{22}$N$_2$O$_6$=434.15.

EXAMPLE 13

(Preparation of 7-butyryloxymethylcamptothecin)

7-Hydroxymethylcamptothecin (378 mg, 1 m-mol) was dissolved in anhydrous dimethylformamide (80 ml) under warming. Anhydrous pyridine (1 ml) and n-butyric anhydride (1 ml, about 8 eq.) were added to this solution and the mixture was stirred for 4 hours at 60° C. After completion of the reaction, 10 ml of ethanol were added to the reaction mixture with stirring for a while to effect decomposition of the excess of the anhydride and the solvents were then removed by distillation under reduced pressure. The residue was purified by way of column chromatography (chloroform) through silica gel (10 g) followed by recrystallization from n-hexane-chloroform whereby 160 mg (35.7%) of 7-butyryloxymethylcamptothecin were obtained as light yellow white needle crystals. M.P. 252°–254° C.

IR$_{max}^{KBr}$ νcm$^{-1}$: 3350, 1750, 1740, 1665, 1600, 1435, 1155, 770.

NMR (in CDCl$_3$) δ ppm: 0.94(3H, t, J=7 Hz), 1.05(3H, t, J=7 Hz), 1.69(2H, sex, J=7 Hz), 1.91(2H, q, J=7 Hz), 2.42(2H, t, J=7 Hz), 5.28(2H, d, J=16 Hz), 5.44(2H, s), 5.69(2H, s), 5.72(2H, d, J=16 Hz), 7.63(1H, s), 7.58–8.25(4H, m).

MS: m/e 448 [M+] for C$_{25}$H$_{24}$N$_2$O$_6$=448.16.

EXAMPLE 14

(Preparation of 7-octanoyloxymethylcamptothecin)

7-Hydroxymethylcamptothecin (200 mg, 0.53 m-mol) was dissolved in warmed anhydrous pyridine (50 ml). n-Octanoyl chloride (260 mg, 3 eq) was added to this solution and the mixture was stirred for 2 hours at 80° C. The solvent was then distilled off under reduced pressure and the residue was taken up in chloroform (100 ml). The solution was washed at 0° C. first with a 5% aqueous solution (50 ml) of sodium carbonate and a saturated edible salt solution (50 ml) and the chloroform layer was dried with anhydrous magnesium sulfate. The solvent was eliminated by distillation and the residue was purified by way of column chromatography (chloroform) through silica gel (7 g) followed by recrystallization from n-hexane-chloroform whereby 79 mg (29.6%) of 7-octanoyloxymethylcamptothecin were obtained as light yellow white needle crystals. M.P. 188°–190° C.

IR$_{max}^{KBr}$ νcm$^{-1}$: 3350, 2910, 1740, 1655, 1590, 1155, 1050, 765.

NMR (in CDCl$_3$) δ ppm: 1.04(3H, t, J=7.5 Hz), 1.24(13H, bs), 1.90 (2H, q, J=7.5 Hz), 2.40(2H, t, J=7 Hz), 5.28 (2H, d, J=17 Hz), 5.45(2H, s), 5.67(2H, s), 5.71(2H, d, J=17 Hz), 7.61(1H, s), 7.53–8.28(4H, m).

Ms: m/e 504 [M+] for C$_{29}$H$_{32}$N$_2$O$_6$=504.22.

EXAMPLE 15

(Preparation of 7-decanoyloxymethylcamptothecin)

7-Hydroxymethylcamptothecin (200 mg, 0.53 m-mol) was dissolved in warmed anhydrous pyridine (50 ml). n-Decanoyl chloride (300 mg, 3 eq) was added to the solution and the mixture was stirred for 2 hours at 80° C. Thereafter, the solvent was removed by distillation under reduced pressure and the residue was dissolved in chloroform (100 ml). The solution was washed at 0° C. with a 5% aqueous solution (50 ml) of sodium carbonate and saturated aqueous edible salt solution (50 ml) and the chloroform layer was dried with anhydrous magnesium sulfate. The solvent was removed by distillation and the residue was purified by way of column chromatography (chloroform) through silica gel (7 g) followed by recrystallization from n-hexane-chloroform whereby 83 mg (29.5%) of 7-decanoyloxymethylcamptothecin were obtained as light yellow needle crystals. M.P. 219°–221° C.

IR$_{max}^{KBr}$ νcm$^{-1}$: 3220, 2910, 1730, 1655, 1590, 1160, 760.

NMR (in CDCl$_3$) δ ppm: 1.05(3H, t, 7.5 Hz), 1.22(17H, s), 1.91(2H, q, J=7.5 Hz), 2.42(2H, t, J=7 Hz), 5.28(2H, d, J=17 Hz), 5.44(2H, s), 5.68(2H, s), 5.73(2H, d, J=17 Hz), 7.63(1H, s), 7.56–8.25(4H, m).

MS: m/e 532 [M+] for C$_{31}$H$_{36}$N$_2$O$_6$=532.26.

EXAMPLE 16

(Preparation of 7-isovaleroxymethylcamptothecin)

7-Hydroxymethylcamptothecin (200 mg, 0.53 m-mol) was dissolved in warmed anhydrous pyridine (50 ml). Isovaleric chloride (190 mg, 3 eq) was added to the solution and the mixture was stirred for 2 hours at 80° C. Thereafter, the solvent was distilled off under reduced pressure and the residue was dissolved in chloroform (100 ml). The solution was washed at 0° C. with a 5% aqueous solution (50 ml) of sodium carbonate and a saturated aqueous solution (50 ml) of edible salt and the chloroform layer was dried with anhydrous magnesium sulfate. The solvent was removed by distillation and the residue was purified by way of column chromatography (chloroform) through silica gel (7 g) followed by recrystallization from n-hexane-chloroform whereby 110 mg (44.9%) of 7-isovaleroxymethylcamptothecin were obtained as light yellow white crystals. M.P. 240°–242° C.

IR$_{max}^{KBr}$ νcm$^{-1}$: 3450, 2950, 1740, 1650, 1595, 1160, 760.

NMR (in CDCl$_3$) δ ppm: 0.94(6H, d, J=7 Hz), 1.07(3H, t, J=7 Hz), 1.91(2H, q, J=7 Hz), 2.31(2H, d, J=7 Hz), 3.71(1H, m), 5.30(2H, d, J=16 Hz), 5.45(2H, s), 5.69(2H, d, J=16 Hz), 5.72(2H, s), 7.65(1H, s), 7.57–8.27(4H, m).

MS: m/e 462 [M+] for C$_{26}$H$_{26}$N$_2$O$_6$=462.18.

EXAMPLE 17

(Preparation of 7-phenylacetoxymethylcamptothecin)

7-Hydroxymethylcamptothecin (500 mg, 1.32 m-mol) was dissolved in warmed anhydrous dimethylformamide (100 ml). Anhydrous pyridine (1 ml) and phenylacetyl chloride (610 mg, 3 eq) were added to the solution and the mixture was stirred for 2 hours at 80° C. Thereafter, the solvent was removed by distillation under reduced pressure and the residue was dissolved in chloroform (200 ml). The solution was washed at 0° C. with a 5% aqueous solution (100 ml) of sodium carbonate and a saturated aqueous solution (100 ml) of edible salt. The chloroform layer was dried with anhydrous magnesium sulfate and the solvent was removed by distillation. The residue was purified by way of column chromatography (chloroform) through silica gel (10 g) followed by recrystallization from n-hexane-chloroform whereby (160 mg (24.4%) of 7-phenylacetoxymethyl-camptothecin were obtained as light yellow white crystals. M.P. 252°–253° C.

$IR_{max}^{KBr}$ νcm$^{-1}$: 3400, 2970, 1760, 1655, 1600, 1160, 1130, 765.

NMR (in DMSO-d$_6$) δ ppm: 0.89(3H, t, J=7 Hz), 1.89(2H, q, J=7 Hz), 3.77(2H, s), 5.42(2H, s), 5.45(2H, s), 5.79(2H, s), 7.25(5H, s), 7.35(1H, s), 7.60–8.30(4H, m).

MS: m/e 496 [M+] for $C_{29}H_{24}N_2O_6$=496.16.

EXAMPLE 18

(Preparation of camptothecin-7-carboxylic acid)

7-Hydroxymethylcamptothecin (200 mg, 0.529 m-mol) was dissolved in dioxane (300 ml). To this solution was added Jones reagent (2.5 ml, about 5.35 m-ml) and the mixture was stirred for 2 days at room temperature. The precipitate formed was filtered off and the filtrate was evaporated until dryness under reduced pressure. Water (15 ml) was added to the residue and an insoluble matter was collected on a filter and washed thoroughly with water (50 ml). This precipitate was purified by recrystallization from dioxane whereupon camptothecin-7-carboxylic acid was obtained as light yellow crystals having a melting point above 300° C. The yield was 95 mg (45.8%).

$IR\nu_{max}^{KBr}$ cm$^{-1}$: 3450–2670, 1760, 1650, 1595, 1240, 1170, 785.

NMR (CDCl$_3$) δ ppm: 0.91(3H, t, J=7 Hz), 1.90(2H, q, J=7 Hz), 5.31 (2H, s), 5.41(2H, s), 6.50(1H, br s, D$_2$O ex.), 7.30(1H, s), 7.65–8.18(3H, m), 8.76–8.84(1H, m).

MS m/e: 392.0995 [M+] ($C_{21}H_{16}N_2O_6$=392.1002).

$UV\lambda_{max}^{EtOH}$nm: 220, 249(sh), 290, 310, 336(sh), 360, 374.

EXAMPLE 19

(Preparation of ethyl camptothecin-7-carboxylate)

Camptothecin-7-carboxylic acid (40 mg, 0.102 m-mol) was suspended in ethanol (15 ml). Concentrated sulfuric acid (0.5 ml) was added to the suspension and the mixture was refluxed for 36 hours. The ethanol was distilled off under reduced pressure and ice water (100 ml) was added to the residue to form a precipitate which was then collected by filtration. On the other hand, a 5% aqueous solution of potassium carbonate was added in small portions to the filtrate to make the liquid neutral. The liquid was extracted with chloroform (100 ml×3) and the extract was dried with anhydrous magnesium sulfate, filtered and evaporated until dryness under reduced pressure. This residue was combined with the precipitate already collected and purified by recrystallization from ethanol-dioxane whereby ethyl camptothecin-7-carboxylate was obtained as yellow prismatic crystals having a melting point above 300° C. The yield was 26.5 mg (62%).

$IR\nu_{max}^{KBr}$ cm$^{-1}$: 2930, 1775, 1750, 1660, 1590, 1230, 785.

NMR (DMSO-d$_6$) ppm: 0.91(3H, t, J=7.5 Hz), 1.35(3H, t, J=7.5 Hz), 1.90(2H, q, J=7.5 Hz), 4.21(2H, q, J=7.5 Hz), 5.34(2H, s), 5.43(2H, br s), 7.37(1H, s), 7.70–8.70(4H, m).

MS m/e: 420 [M+] ($C_{23}H_{20}N_2O_6$=420.).

EXAMPLE 20

(Preparation of 5-methoxycamptothecin)

5-Hydroxycamptothecin (224 mg, 0.615 m-mol) was dissolved in methanol (40 ml). Boron trifluoride etherate (515 mg, 3.63 m-mol) was added to the solution and the mixture was refluxed for 18 hours. The methanol was removed by distillation under reduced pressure and the residue was shaken with water (100 ml) and further with chloroform (100 ml). The aqueous phase in this case was then extracted with chloroform (100 ml×2) and the chloroform layer was combined with that already obtained in the preceding treatment, dried with anhydrous magnesium sulfate, filtered and evaporated until dryness under reduced pressure. The residue was subjected to column chromatography (2% methanol-chloroform) through silica gel (50 g) to effect separation and purification of the product whereby 159 mg (91.9%) of 5-methoxycamptothecin were obtained as a yellow white solid. Separately, 54 mg of 5-hydroxycamptothecin were recovered.

$IR\nu_{max}^{KBr}$ cm$^{-1}$: 3400, 2980, 1750, 1660, 1600, 1460, 1235, 1165.

NMR (CDCl$_3$) δ ppm: 1.02(3H, t, J=7.5 Hz), 1.92(2H, q, J=7.5 Hz), 3.52(1.5H, s), 3.68(1.5H, s), 5.32.5.72(two 1Hs, dxd, J=19 Hz), 6.75(0.5H, s), 6.89(0.5H, s) 7.60(1H, br s), 7.50–8.40(4H, m), 8.41(1H, br s).

MS m/e 378.1214 [M+] ($C_{21}H_{18}N_2O_5$=378.1209.).

$UV\lambda_{max}^{EtOH}$ nm: 249(sh), 258, 297, 337(sh), 356, 372(sh).

EXAMPLE 21

(Preparation of 5-n-butoxycamptothecin)

5-Hydroxycamptothecin (160 mg, 0.439 m-mol) was dissolved in n-butanol (20 ml). Boron trifluoride etherate (1 ml) was added to the solution and the mixture was refluxed for 1.5 hours. The reaction mixture was evaporated until dryness under reduced pressure and the residue was shaken with water (100 ml) and further with chloroform (150 ml). The chloroform layer was dried with anhydrous magnesium sulfate, filtered and evaporated until dryness under reduced pressure. The residue was subjected to column chromatography (chloroform) through silica gel (30 g) to effect separation and purification of the product whereby 5-n-butoxycamptothecin was obtained as a light yellow solid. The yield was 121 mg (65.5%).

$IR\nu_{max}^{KBr}$ cm$^{-1}$: 3400, 2960, 1765, 1670, 1620, 1465, 1420, 1165.

NMR (CDCl$_3$-DMSO-d$_6$) δ ppm: 1.02(3H, t, J=7.5 Hz), 0.86–1.80(7H, br m), 1.94(2H, q, J=7.5 Hz), 4.00(2H, m), 5.22, 5.69(two 1Hs, dxd, J=17.5 Hz), 6.77(0.5H, s), 6.87(0.5H, s), 7.33–8.40(4H, m), 7.61(1H, s), 8.41(1H, s).

EXAMPLE 22

(Preparation of 20-O-acetyl-5-acetoxycamptothecin)

5-Hydroxycamptothecin (30 mg, 0.082 m-mol) was dissolved in pyridine (10 ml). Acetic anhydride (16 mg, 0.153 m-mol) was added to the solution and the mixture was stirred for 3 hours at room temperature. The reaction mixture was evaporated until dryness under reduced pressure and the residue was shaken with water (50 ml) and further with chloroform (50 ml). The chloroform layer was dried with anhydrous magnesium sulfate, filtered and evaporated until dryness under reduced pressure. The residue was subjected to thin layer chromatography (2% methanol-chloroform) to effect separation of the products whereby 14 mg (41.8%) of an isomer of 5-acetoxycamptothecin having an Rf value of 0.15, 12 mg (35.9%) of another isomer having an Rf value of 0.20 and 8 mg (21.7%) of 20-O-acetyl-5-acetoxycamptothecin were obtained.

(1) 5-acetoxycamptothecin having an Rf value of 0.15:

M.P. 202°–205° C. (n-hexane-chloroform).

IR$\nu_{max}^{KBr}$ cm$^{-1}$: 3400, 1760, 1670, 1620, 1160.

NMR (CDCl$_3$) δ ppm: 1.06(3H, t, J=7 Hz), 1.91(2H, q, J=7 Hz), 2.195(3H, s), 5.22, 5.65(two 1 Hs, dxd, J=16.3 Hz), 7.62(1H, s), 7.91(1H, s), 7.68–8.26(4H, m), 8.45(1H, s).

UV$\lambda_{max}^{EtOH}$ nm: 215, 223(sh), 252, 257, 297, 340(sh), 357, 372.

MS m/e: 406.1176 [M+] (C$_{22}$H$_{18}$N$_2$O$_6$=406.1158.).

$[\alpha]_D^{25}$=+117.3° (C=5.2×10$^{-3}$, EtOH).

(2) 5-acetoxycamptothecin having an Rf value of 0.20:

M.P. 258°–261° C. (n-hexane-chloroform).

IR$\nu_{max}^{KBr}$ cm$^{-1}$: 3400, 1760, 1670, 1625, 1165.

NMR (in CDCl$_3$) δ ppm: 1.04(3H, t, J=7 Hz), 1.90(2H, q, J=7 Hz), 2.192(3H, s), 5.22, 5.67(two 1Hs, dxd, J=16.6 Hz), 7.62(1H, s), 7.96(1H, s), 7.70–8.30(4H, m), 8.46(1H, s).

UV$\lambda_{max}^{EtOH}$ nm: 215, 223(sh), 252, 257, 296, 340(sh), 357, 372(sh).

MS m/e: 406.1134 [M+].

$[\alpha]_D^{25}$=−123° (C=3.33×10$^{-3}$, EtOH).

(3) 20-O-acetyl-5-acetoxycamptothecin:

Rf=0.30

IR$\nu_{max}^{KBr}$ cm$^{-1}$: 2930, 1765(vs), 1670, 1625, 1240.

NMR (in CDCl$_3$) δ ppm: 1.00(3H, m), 2.00(2H, m), 2.10(3H, s), 2.19(1.5H, s), 2.25(1.5H, s), 5.30 (0.5H, d, J=19 Hz), 5.31(0.5H, d, J=19 Hz), 5.61(1H, d, J=19 Hz), 7.10(0.5H, s), 7.12(0.5H, s), 7.50–8.30(5H, m), 8.50(1H, br s).

EXAMPLE 23

(Preparation of 5-benzoyloxycamptothecin)

5-Hydroxycamptothecin (200 mg, 0.549 m-mol) was dissolved in pyridine (10 ml). To this solution was added under agitation benzoyl chloride (180 mg, 1.28 m-mol) in small portions over 5 hours at room temperature. After addition of the benzoyl chloride, the agitation was continued for one hour. The reaction mixture was then evaporated until dryness under reduced pressure and the residue was taken up in water (50 ml). Insoluble matters were collected by filtration and dissolved in chloroform (100 ml) and the chloroform solution was dried with anhydrous magnesium sulfate, decolored with active carbon, filtered and evaporated until dryness under reduced pressure. The residue was purified by recrystallization from n-hexane-chloroform whereupon 5-benzoyloxycamptothecin was obtained as light yellow prismatic crystals. The yield was 154 mg (60%).

IR$\nu_{max}^{KBr}$ cm$^{-1}$: 3400, 3080, 2980, 1760, 1740, 1670, 1610, 1460, 1410, 1270.

NMR (CDCl$_3$-DMSO-d$_6$) δ ppm: 1.02(3H, br t, J=7.5 Hz), 2.00(2H, br q, J=7.5 Hz), 5.23, 5.56(two 1Hs, dxd, J=17.5 Hz), 7.33–8.40(9H, m), 7.53(1H, s), 7.21(0.5H, s), 7.32(0.5H, s), 8.72(1H, s).

MS m/e: 468.1296 [M+] (C$_{27}$H$_{20}$N$_2$O$_6$=468.1314.).

EXAMPLE 24

(Preparation of 7-methylcamptothecin)

Ferrous sulfate heptahydrate (4.17 g, 15 m-mol) and ethanol (3 ml, 60 m-mol) were dissolved in water (30 ml). Camptothecin (700 mg, 2 m-mol) was suspended in the solution and dissolved therein by adding concentrated sulfuric acid (15 ml) in small portions to the suspension. To the mixture was added dropwise under ice-cooling and agitation a 30% aqueous solution of hydrogen peroxide (1.63 ml, 16 m-mol). After addition of the hydrogen peroxide, the mixture was stirred for 6 hours at room temperature. To the reaction mixture was added ferrous sulfate heptahydrate (2.0 g, 7.2 m-mol) and then was added dropwise under ice-cooling and agitation a 30% aqueous solution of hydrogen peroxide (1 ml, 9.8 m-mol). The agitation was continued for 15 hours at room temperature. To complete the reaction, additional ferrous sulfate heptahydrate (4.2 g, 15 m-mol) and a 30% aqueous solution of hydrogen peroxide (1.5 ml, 14.7 m-mol) were added to the reaction mixture and the whole was stirred for 8 hours at room temperature. The reaction mixture was diluted with ice water (2.5 liters) and extracted with chloroform (3 liters). The chloroform layer was dried with anhydrous magnesium sulfate, filtered and evaporated until dryness under reduced pressure. The residue was purified by way of column chromatography (chloroform) through silica gel (10 g) followed by recrystallization from n-hexane-chloroform whereby 127 mg (17.5%) of the objective compound were obtained as yellow needle crystals. M.P. 280°–281° C.

IR$\nu_{max}^{KBr}$ cm$^{-1}$: 3350, 2920, 1755, 1650, 1600, 1470, 1155, 765.

NMR (in DMSO-d$_6$) δ ppm: 0.91(3H, t, J=7.5 Hz), 1.88(2H, q, J=7.5 Hz), 2.79(3H, s), 5.26(2H, s), 5.41(2H, s), 6.43(1H, s, D$_2$O,ex), 7.34(1H, s), 7.57–8.32 (4H, m).

MS m/e: 362 [M+] (C$_{21}$H$_{18}$N$_2$O$_4$=362.37).

EXAMPLE 25

(Preparation of 7-methylcamptothecin)

Ferrous sulfate heptahydrate (2.0 g, 7 m-mol) was dissolved in water (15 ml) and acetic acid (1.5 ml, 25 m-mol) was added thereto. Camptothecin (500 mg, 1.43 m-mol) was suspended in the resultant solution and dissolved therein by addition of concentrated sulfuric acid (8 ml) in small portions. To this solution was added dropwise under ice-cooling and agitation tert-butyl hydroperoxide (900 mg, 10 m-mol) in small portions. After addition of the tert-butyl hydroperoxide, the agitation was continued for one hour at room temperature. The reaction mixture was diluted with ice water (500 ml) and extracted with chloroform (1.5 l). The chloroform layer was dried with anhydrous magnesium sulfate, filtered and evaporated until dryness under reduced pressure. The residue was washed thoroughly with acetone to obtain 440 mg (84.4%). The crude crystals were purified by recrystallization from pyridine-methanol whereby 300 mg (57.6%) of the objective compound were obtained as light yellow white needle crystals.

The analytical data of this product were identical with those of the compound obtained in Example 24.

EXAMPLE 26

(Preparation of 7-ethylcamptothecin)

In an aqueous solution of sulfuric acid (15 ml of concentrated sulfuric acid in 30 ml of water) were dissolved camptothecin (1.00 g, 2.87 m-mol), ferrous sulfate heptahydrate (5.60 g, 20.1 m-mol) and 1-propanol (6 ml, 86.1 m-mol). To this solution was added dropwise under ice-cooling and agitation a 30% aqueous solution of hydrogen peroxide (2.1 ml, 20.1 m-mol) in small portions. After addition of the hydrogen peroxide, the agitation was continued for one hour at room temperature. The reaction was diluted with ice water (2 l) and extracted with chloroform (2.5 l). The chloroform layer was dried with anhydrous magnesium sulfate, filtered and evaporated until dryness under reduced pressure. The residue was subjected to column chromatography (chloroform) through silica gel (15 g) to effect separation and purification of the product which was then recrystallized from n-hexane-chloroform whereby 265 mg (25.3%) of the objective compound were obtained as light yellow white needle crystals. M.P. 258°–261° C.

IR$\nu_{max}^{KBr}$ cm$^{-1}$: 3370, 2920, 1750, 1650, 1600, 1460, 1150, 760.

NMR (in DMSO-d$_6$-CDCl$_3$) δ: 0.97(3H, t, J=7 Hz), 1.39(3H, t, J=7 Hz), 1.91(2H, q, J=7 Hz), 3.21(2H, q, J=7 Hz), 5.21(2H, s), 5.24(1H, d, J=16 Hz), 5.57 (1H, d, J=16 Hz), 7.49(1H, s), 7.44–8.21 (4H, m).

MS m/e: 376.1399 [M+] (C$_{22}$H$_{20}$N$_2$O$_4$=376.1422).

EXAMPLE 27

(Preparation of 7-ethylcamptothecin)

Ferrous sulfate heptahydrate (350 mg, 1.25 m-mol) was dissolved in water (10 ml). Propionaldehyde (144 mg, 2.48 m-mol) was added to the solution and dissolved therein by addition of acetic acid (10 ml). Camptothecin (175 mg, 0.5 m-mol) was suspended in the solution and then dissolved therein by addition of concentrated sulfuric acid (2 ml) in small portions. To this solution was added dropwise under ice-cooling and agitation a 30% aqueous solution of hydrogen peroxide (144 mg, 1.27 m-mol) in small portions. The agitation was continued for 15 minutes under ice-cooling. The reaction mixture was diluted with ice water (500 ml) and then extracted with chloroform (800 ml). The chloroform layer was dried with magnesium sulfate, filtered and evaporated until dryness under reduced pressure. The residue was subjected to column chromatography (chloroform) through silica gel (10 g) to effect separation and purification of the product whereby 105 mg (55.8%) of the objective compound were obtained as light yellow white crystals. The analytical data of the resultant product were identical with those of the product obtained in Example 26.

EXAMPLE 28

(Preparation of 7-ethylcamptothecin)

Ferrous sulfate heptahydrate (1.0 g, 3.59 m-mol) was dissolved in water (10 ml). Diethyl ketone (1.29 g, 15 m-mol) was added to this solution and acetic acid (6 ml) was then dissolved therein. Camptothecin (175 mg, 0.5 m-mol) was suspended in this solution and then dissolved by addition of concentrated sulfuric acid (2 ml). To this solution was then added dropwise under ice-cooling and agitation a 30% aqueous solution of hydrogen peroxide (560 mg, 5 m-mol) in small portions. After addition of the hydrogen peroxide, the mixture was agitated for 48 hours at room temperature. The reaction mixture was diluted with ice water (500 ml) and extracted with chloroform (500 ml). The chloroform layer was dried with magnesium sulfate, filtered and evaporated until dryness under reduced pressure. The residue was subjected to column chromatography (chloroform) through silica gel (10 g) to effect separation of the product whereby 17 mg (13.8%) of the objective compound and 61 mg of unreacted camptothecin were obtained.

The analytical data of the resultant 7-ethylcamptothecin were identical with those of the compound obtained in Example 26.

EXAMPLE 29

(Preparation of 7-ethylcamptothecin)

Ferrous sulfate heptahydrate (1.20 g, 4.31 m-mol) and propionic acid was dissolved in water (15 ml). Camptothecin (300 mg, 0.862 m-mol) was suspended in the solution and dissolved therein by addition of concentrated sulfuric acid (6 ml) in small portions. To this solution was added dropwise under ice-cooling and agitation a 30% aqueous solution of hydrogen peroxide (1 ml, 9.81 m-mol) in small portions over the period of about 10 minutes. After addition of the hydrogen peroxide, the agitation was continued for 16 hours at room temperature. The reaction mixture was diluted with ice water (300 ml) and extracted with chloroform (400 ml). The chloroform layer was dried with magnesium sulfate, filtered and evaporated until dryness under reduced pressure. The residue was subjected to column chromatography (chloroform) through silica gel (10 g) to effect separation and purification of the product whereby 73 mg (22.5 g) of the objective compound were obtained as a yellow white solid.

The analytical data of this compound were identical with those of the compound obtained in Example 26.

EXAMPLE 30

(Preparation of 7-propylcamptothecin)

Ferrous sulfate heptahydrate (2.8 g, 10.1 m-mol) and 1-butanol (3 ml, 43 m-mol) were dissolved in water (30 ml). Camptothecin (500 mg, 1.43 m-mol) was suspended in the solution and dissolved therein by addition of concentrated sulfuric acid (15 ml). To this solution was added dropwise under ice-cooling and agitation a 30% aqueous solution of hydrogen peroxide (1.1 ml, 10.1 m-mol) in small portions. The agitation was continued for 4 hours at room temperature. The reaction mixture was diluted with ice water (1.5 l) and extracted with chloroform (2 l). The chloroform layer was dried with magnesium sulfate, filtered and evaporated until dryness under reduced pressure. The residue was subjected to column chromatography (chloroform) through silica gel (15 g) to effect separation and purification of the product which was then recrystallized from n-hexane-chloroform whereby 110 mg (21.0%) of the objective compound were obtained as light yellow white needle crystals. M.P. 260°–261° C.

IR$\nu_{max}^{KBr}$ cm$^{-1}$: 3400, 2930, 1745, 1650, 1600, 1455, 1155, 760.

NMR (CDCl$_3$) δ: 1.03(3H, t, J=7 Hz), 1.08(3H, t, J=8 Hz), 1.25–2.05(4H, m), 3.26(2H, t, J=8 Hz), 5.24(2H, s), 5.52(2H, dxd, J=17 Hz), 7.67(1H, s), 7.55–8.29(4H, m).

MS m/e: 390 [M+] (C$_{25}$H$_{22}$N$_2$O$_4$=390.43).

EXAMPLE 31

(Preparation of 7-propylcamptothecin)

Ferrous sulfate heptahydrate (800 mg, 2.88 m-mol) was dissolved in water (10 ml). Butyraldehyde (260 mg, 3.61 m-mol) was added to the solution and dissolved therein by the addition of acetic acid (17 ml). Camptothecin (500 mg, 1.44 m-mol) was suspended in the solution and dissolved therein by the addition of concentrated sulfuric acid (2 ml) in small portions. To this solution was added dropwise under ice-cooling and agitation a 30% aqueous solution of hydrogen peroxide (333 mg, 2.93 m-mol) in small portions. The agitation was continued for 20 minutes under ice-cooling. The reaction mixture was diluted with ice water (1 l) and extracted with chloroform (1 l). The chloroform layer was dried with magnesium sulfate, filtered and evaporated until dryness under reduced pressure. The residue was subjected to column chromatography (chloroform) through silica gel (15 g) to effect separation and purification of the product whereby 333 mg (59.3%) of the objective compound was obtained as yellow white crystals. Purification of the crude product by recrystallization from ethanol gave light yellow prismatic crystals. The analytical data of this product were identical with those of the product obtained in Example 30.

EXAMPLE 32

(Preparation of 7-butylcamptothecin)

Ferrous sulfate heptahydrate (3.0 g, 10.7 m-mol) was dissolved in water (30 ml). Camptothecin (500 mg, 1.43 m-mol) was suspended in the solution and dissolved therein by addition of concentrated sulfuric acid (20 ml). To this solution was added 1-amyl alcohol (4.6 ml, 43 m-mol) and then was added dropwise under ice-cooling and agitation a 30% aqueous solution of hydrogen peroxide (1.1 ml, 10.7 m-mol) in small portions. After addition of the hydrogen peroxide, the agitation was continued for 4 hours at room temperature. The reaction mixture was diluted with ice water (1.5 l) and extracted with chloroform (2 l). The chloroform layer was dried with magnesium sulfate, filtered and evaporated until dryness under reduced pressure. The residue was subjected to column chromatography (chloroform) through silica gel (10 g) to effect separation and purification of the product which was further purified by recrystallization from n-hexane-chloroform whereby 54 mg (9.3%) of the objective compound was obtained as light yellow white needle crystals. M.P. 206°–207° C.

IR$\nu_{max}^{KBr}$ cm$^{-1}$: 3350, 2930, 1745, 1680, 1600, 1450, 1150, 755.

NMR (CDCl$_3$) δ: 0.80–2.04(12H, m), 3.14(2H, t, J=7 Hz), 5.20(2H, s), 5.26(1H, d, J=17 Hz), 5.73(1H, d, J=17 Hz), 7.62(1H, s), 7.28–7.88(2H, m), 7.96–8.26(2H, m).

MS m/e: 404 [M+] (C$_{24}$H$_{24}$N$_2$O$_4$=404).

EXAMPLE 33

(Preparation of 7-butylcamptothecin)

Ferrous sulfate heptahydrate (300 mg, 1.07 m-mol) was dissolved in water (10 ml). This solution was overlaid with n-amyl alcohol (310 μl, 2.86 m-mol) and dimethylformamide (6 ml) was added to dissolve the n-amyl alcohol in the solution. Camptothecin (50 mg, 0.143 m-mol) was suspended in the solution and dissolved by the addition of concentrated sulfuric acid (1.5 ml). To this solution was added dropwise under ice-cooling and agitation a 30% aqueous solution of hydrogen peroxide (110 μl, 1.07 m-mol) in small portions. After addition of the hydrogen peroxide, the mixture was stirred for 4 hours at room temperature. The reaction mixture was diluted with ice water (100 ml) and extracted with chloroform (300 ml). The chloroform layer was dried with magnesium sulfate, filtered and evaporated until dryness under reduced pressure. The residue was subjected to column chromatography through silica gel (4 g) to effect separation and purification of the product which was further purified by recrystallization from n-hexane-chloroform whereby 18 mg (32%) of the objective compound were obtained as light yellow white needle crystals. The analytical data of this compound were identical with those of the compound obtained in Example 32.

EXAMPLE 34

(Preparation of 7-heptylcamptothecin)

Ferrous sulfate heptahydrate (800 mg, 2.88 m-mol) was dissolved in water (10 ml). Octanal (459 mg, 3.56 m-mol) was added to the solution and dissolved therein by the addition of acetic acid (20 ml). Camptothecin (500 mg, 1.44 m-mol) was suspended in this solution and dissolved therein by adding portionwise concentrated sulfuric acid (4 ml) to the suspension. To this solution was added dropwise under ice-cooling and agitation a 30% aqueous solution of hydrogen peroxide (333 mg, 2.94 m-mol) in small portions. After addition of the hydrogen peroxide, the agitation was continued for 15 minutes under ice-cooling. The reaction mixture was diluted with ice water (1 l) and extracted with chloroform (600 ml). The chloroform layer was dried with magnesium sulfate, filtered and evaporated until dryness under reduced pressure. The residue was subjected to column chromatography (chloroform) through silica gel (15 g) to effect separation and purification of the product whereby 334 mg (53.5%) of the objective compound were obtained as a yellow white solid. Recrystallization of the solid from ethanol gave yellow white needle crystals. M.P. 245°–246° C.

IR$\nu_{max}^{KBr}$ cm$^{-1}$: 3380, 2920, 1750, 1655, 1600, 1460, 1160, 763.

NMR (in CDCl$_3$) δ: 0.80–2.05(18H, m), 3.16(2H, br, t, J=8 Hz), 5.23(2H, s), 5.30(1H, d, J=17 Hz), 5.72(1H, d, J=17 Hz), 7.65(1H, s), 7.30–7.85(2H, m), 8.02–8.30(2H, m).

MS m/e: 446 [M+] (C$_{27}$H$_{30}$N$_2$O$_4$=446.22).

EXAMPLE 35

(Preparation of 7-nonylcamptothecin)

Ferrous sulfate heptahydrate (800 mg, 2.88 m-mol) was dissolved in water (10 ml). n-Decylaldehyde (560 mg, 2.94 m-mol) was added to the solution and dissolved therein by the addition of acetic acid (32 ml). Camptothecin (500 mg, 1.44 m-mol) was suspended in the solution and dissolved therein by adding concentrated sulfuric acid (4 ml) portionwise to the suspension. To this solution was added dropwise under ice-cooling and agitation a 30% aqueous solution of hydrogen peroxide (333 mg, 2.94 m-mol) in small portions. After addition of the hydrogen peroxide, the agitation was continued for 30 minutes under ice-cooling. The reaction mixture was diluted with ice water (1 l) and extracted which chloroform (1 l). The chloroform layer was dried with magnesium sulfate, filtered and evaporated until dryness under reduced pressure. The residue was subjected to column chromatography (chloroform) through silica gel to effect separation and purification of the product whereby 261 mg (38.3%) of the objective compound were obtained as a yellow white solid. Purification of this compound by recrystallization from methanol gave yellow white needle crystals. M.P. 205°–207° C.

IR$\nu_{max}^{KBr}$ cm$^{-1}$: 3420, 2930, 1750, 1655, 1595, 1460, 1160, 762.

NMR (in CDCl$_3$) δ: 0.78–2.02(22H, m), 3.16(2H, br, t, J=7 Hz), 5.24(2H, s), 5.30(1H, d, J=17 Hz), 5.72(1H, d, J=17 Hz), 7.68(1H, s), 7.50–7.90(2H, m), 8.02–8.30(2H, m).

MS m/e: 474 [M+] (C$_{29}$H$_{34}$N$_2$O$_4$=474.25).

EXAMPLE 36

(Preparation of 7-isobutylcamptothecin)

Ferrous sulfate heptahydrate (2.80 g, 10.1 m-mol) was dissolved in water (30 ml). The solution was overlaid with isoamyl alcohol (3.5 ml, 39 m-mol) and dimethylformamide (10 ml) was added to dissolve the isoamyl alcohol in the solution. Camptothecin (500 mg, 1.43 m-mol) was suspended in this solution and dissolved therein by adding concentrated sulfuric acid (15 ml) to the suspension. To this solution was added dropwise under ice-cooling and agitation a 30% aqueous solution of hydrogen peroxide (1.1 ml, 10.1 m-mol) in small portions. After addition of the hydrogen peroxide, the agitation was continued for 40 minutes at room temperature. The reaction was diluted with ice water (1.5 l) and extracted with chloroform (1.5 l). The chloroform layer was dried with magnesium sulfate, filtered and evaporated until dryness under reduced pressure. The residue was subjected to column chromatography (chloroform) through silica gel (15 g) to effect separation and purification of the product which was further purified by recrystallization from n-hexane-chloroform whereby 95 mg (16.7%) of the objective compound were obtained as light yellow white needle crystals. M.P. 198°–200° C.

IR$\nu_{max}^{KBr}$ cm$^{-1}$: 3400, 2930, 1740, 1650, 1595, 1450, 1155, 760.

NMR (CDCl$_3$) δ: 1.07(3H, t, J=7 Hz), 1.07(6H, d, J=7 Hz), 1.93(2H, q, J=7 Hz), 2.12–2.40(1H, m), 3.09(2H, d, J=7 Hz), 5.28(2H, s), 5.54(2H, dxd, J=17 Hz), 7.68(1H, s), 7.55–8.29(4H, m).

MS: m/e 404 [M+] (C$_{24}$H$_{24}$N$_2$O$_4$=404).

EXAMPLE 37

(Preparation of 7-benzylcamptothecin)

Ferrous sulfate heptahydrate (3.40 g, 12.2 m-mol) was dissolved in water (30 ml). The solution was overlaid with β-phenethyl alcohol (3.20 g, 28.6 m-mol) and acetic acid (27 ml) was added to dissolve the β-phenethyl alcohol in the solution. Camptothecin (500 mg, 1.43 m-mol) was suspended in the solution and dissolved therein by the addition of concentrated sulfuric acid (30 ml) to the suspension. To this mixture was added dropwise under ice-cooling and agitation a 30% aqueous solution of hydrogen peroxide (1.5 ml, 14.7 m-mol) in small portions. After addition of the hydrogen peroxide, the agitation was continued for 16 hours at room temperature. The reaction mixture was diluted with ice water (1.5 l) and extracted with chloroform (1.5 l). The chloroform layer was dried with magnesium sulfate, filtered and evaporated until dryness under reduced pressure. The residue was washed thoroughly with n-hexane and subjected to column chromatography (chloroform) through silica gel (10 g) to effect separation and purification of the product which was further purified by recrystallization from n-hexane-chloroform whereby 202 mg (50.6%) of the objective compound were obtained as light yellow white needle crystals. M.P. 263°–265° C.

IR$\nu_{max}^{KBr}$ cm$^{-1}$: 3360, 2800, 1735, 1650, 1590, 1440, 1145, 755, 695.

NMR (in CDCl$_3$) δ: 1.03(3H, t, J=7.5 Hz), 1.89(2H, q, J=7.5 Hz), 4.58(2H, s), 5.14(2H, s), 5.26(1H, d, J=16.2 Hz), 5.73(1H, d, J=16.2 Hz), 7.00–7.34(5H, m), 7.68(1H, s), 7.55–8.32(4H, m).

MS: m/e 438 [M+] (C$_{27}$H$_{22}$N$_2$O$_4$=438.47).

EXAMPLE 38

(Preparation of 7-β-phenethylcamptothecin)

In an aqueous solution of sulfuric acid (10 ml of concentrated sulfuric acid in 25 ml of water) were dissolved camptothecin (350 mg, 1 m-mol) and ferrous sulfate heptahydrate (2.0 g, 7.2 m-mol). The solution was overlaid with 3-phenylpropanol (1.5 g, 11.0 m-mol) and dimethylformamide (10 ml) was added to dissolve the 3-phenylpropanol in the solution. To this mixture was added dropwise under ice-cooling and agitation a 30% aqueous solution of hydrogen peroxide (740 μl, 7.2 m-mol) in small portions. After addition of the hydrogen peroxide, the mixture was stirred for 20 hours at room temperature. To this reaction mixture were added ferrous sulfate heptahydrate (2.0 g, 7.2 m-mol), 3phenylpropanol (1.5 g, 11.0 m-mol) and dimethylformamide (35 ml). To the mixture was added under ice-cooling and agitation a 30% aqueous solution of hydrogen peroxide (740 μl, 7.2 m-mol). The mixture was further stirred for 20 hours at room temperature. The reaction mixture was diluted with ice water (1.5 l) and extracted with chloroform (2.0 l). The chloroform phase was dried with magnesium sulfate, filtered and evaporated until dryness under reduced pressure. The residue was subjected to column chromatography (chloroform) through silica gel (10 g) to effect separation and purification of the product which was further purified by recrystallization from n-hexane-chloroform whereby 66 mg (14.2%) of the objective compound were obtained as light yellow white needle crystals. M.P. 260°–262° C.

IR$\nu_{max}^{KBr}$ cm$^{-1}$: 3370, 2920, 1745, 1655, 1600, 1450, 1155, 755, 700.

NMR (in CDCl$_3$) δ: 1.02(3H, t, J=7.5 Hz), 1.89(2H, q, J=7.5 Hz), 3.47(2H, t, J=7 Hz), 3.80(2H, t, J=7 Hz), 4.78(2H, s), 5.24(1H, d, J=17 Hz), 5.70(1H, d, J=17 Hz), 6.98–7.40(5H, m), 7.61(1H, s), 7.51–8.38(4H, m).

MS: m/e 452 [M+] (C$_{28}$H$_{24}$N$_2$O$_4$=452.49).

EXAMPLE 39

(Preparation of 7-isopropylcamptothecin)

Ferrous sulfate heptahydrate (2.0 g, 7.5 m-mol) was dissolved in water (20 ml). The solution was overlaid with isobutanol (2.75 ml, 30 m-mol) and acetic acid (6 ml) was added to dissolve the isopropanol in the solution. Camptothecin (350 mg, 1 m-mol) was suspended in the solution and dissolved therein by addition of concentrated sulfuric acid (17 ml) to the suspension. To this solution was added dropwise under ice-cooling and agitation a 30% aqueous solution of hydrogen peroxide (760 μl, 7.5 m-mol) in small portions. After addition of the hydrogen peroxide, the mixture was stirred for 30 minutes at room temperature. The reaction mixture was diluted with ice water (1 l) and extracted with chloroform (1.5 l). The chloroform layer was dried with magnesium sulfate, filtered and evaporated until dryness under reduced pressure. The residue was subjected to column chromatography (chloroform) through silica gel (10 g) to effect separation and purification of the product which was further purified by recrystallization from n-hexane-chloroform whereby 128 mg (32.8%) of the objective compound were obtained as light yellow white needle crystals. M.P. 258°–259° C.

IR$\nu_{max}^{KBr}$ cm$^{-1}$: 3400, 2950, 1750, 1645, 1595, 1460, 1155, 760.

NMR (in CDCl$_3$) δ: 1.04(3H, t, J=7.5 Hz), 1.54(6H, d, J=7 Hz), 1.90(2H, q, J=7.5 Hz), 4.00(1H, heptet, J=7 Hz), 5.29(1H, d, J=17 Hz), 5.37(2H, s), 5.75(1H, d, J=17 Hz), 7.63(1H, s), 7.45–8.36(4H, m).

MS: m/e 390 [M+] (C$_{23}$H$_{22}$N$_2$O$_4$=390).

EXAMPLE 40

(Preparation of 7-cyclohexyl camptothecin)

Ferrous sulfate heptahydrate (3.0 g, 10.73 m-mol) was dissolved in water (30 ml). The solution was overlaid with cyclohexylmethanol (1.63 ml, 14.3 m-mol) and acetic acid (22 ml) was added with stirring to dissolve the cyclohexylmethanol in the solution. Camptothecin (500 mg, 1.43 m-mol) was suspended in this solution and dissolved therein by adding concentrated sulfuric acid (8 ml) to the suspension. To this mixture was added dropwise under ice-cooling and agitation a 30% aqueous solution of hydrogen peroxide (1.1 ml, 10.73 m-mol) in small portions. After addition of the hydrogen peroxide, the agitation was continued for 30 minutes at room temperature. The reaction mixture was diluted with ice water (1 l) and extracted with chloroform (1.5 l). The chloroform layer was dried with magnesium sulfate, filtered, and evaporated until dryness under reduced pressure. The residue was subjected to column chromatography (chloroform) through silica gel (10 g) to effect separation and purification of the product which was further purified by recrystallization from n-hexane-chloroform whereby 181 mg (29.4%) of the objective compound were obtained as light yellow white needle crystals. M.P. 260°–261° C.

IR$\nu_{max}^{KBr}$ cm$^{-1}$: 3380, 2920, 1745, 1655, 1595, 1440, 1155, 765.

NMR (in CDCl$_3$) δ: 1.04(3H, t, J=8 Hz), 1.20–2.18(12H, m), 3.70(1H, m), 5.30(1H, d, J=17 Hz), 5.39(2H, s), 5.72(1H, d, J=17 Hz), 7.67(1H, s), 7.50–7.85(2H, m), 8.16–8.27(2H, m).

MS: m/e 430 [M+] (C$_{26}$H$_{26}$N$_2$O$_4$=430.19).

It is understood that the preceding representative examples may be varied within the scope of the present specification, both as to reactants and reaction conditions, by one skilled in the art to achieve essentially the same results.

As many widely different embodiments of this invention may be made without departing from the spirit and scope thereof, it is to be understood that this invention is not limited to the specific embodiments thereof except as defined in the appended claims.

What is claimed is:

1. A camptothecin derivative of the formula:

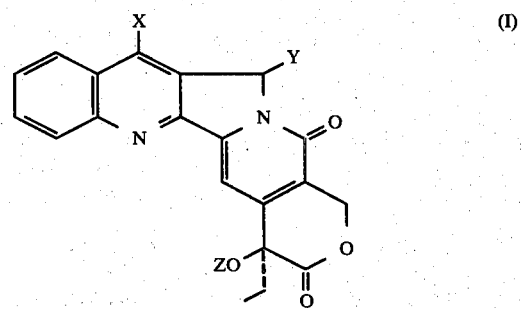

(I)

wherein X is H, CH$_2$OH, COOH, a straight or branched chain alkyl group with 1–18 carbon atoms, a cycloalkyl group with 5–7 carbon atoms, a phenylalkyl group having 1 to 3 carbon atoms in the alkylene portion thereof, or the group CH$_2$OCOR$^1$ or COOR$^2$ where R$^1$ is a straight or branched chain alkyl group with 1–17 carbon atoms, trifluoromethyl, phenyl, a phenylalkyl group having 1 to 2 carbon atoms in the alkylene portion thereof or the group HOOC—(CH$_2$)$_n$ where n is an integer of 2 to 4 and where R$^2$ is a lower alkyl group; Y is H, OH or OR$^3$, where R$^3$ is a lower alkyl group, an alkanoyl group with 1–5 carbon atoms, benzoyl or a phenylalkanoyl group with 1–2 carbon atoms in the alkylene portion thereof; and Z is H, acetyl or trifluoroacetyl; with the proviso (1) that when X is CH$_2$OH, the straight or branched alkyl group, the cycloalkyl group or the phenylalkyl group, both Y and Z are H, (2) that when X is CH$_2$OCOR$^1$ or COOR$^2$, Y is H, (3) that when Y is OH, both X and Z are H, and (4) that when Y is OR$^3$, X is H; or a water-soluble alkali metal salt thereof.

2. 7-Hydroxymethylcamptothecin.

3. 5-Hydroxycamptothecin.

4. A camptothecin derivative of the formula:

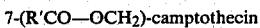

7-(R'CO—OCH$_2$)-camptothecin wherein R' is a straight or branched chain alkyl group with 1–10 carbon atoms, phenyl or a phenylalkyl group with 1–2 carbon atoms in the alkylene portion thereof or the group HOOC—(CH$_2$)$_n$ where n is an integer of 2 to 4.

5. A camptothecin derivative of the formula:

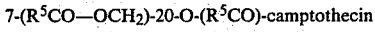

7-(R$^5$CO—OCH$_2$)-20-O-(R$^5$CO)-camptothecin wherein the two R$^5$'s are identical with each other and each represents methyl or trifluoromethyl.

6. A camptothecin derivative of the formula:

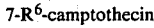

7-R$^6$-camptothecin wherein R$^6$ is a straight or branched chain alkyl group with 1–10 carbon atoms or a cycloalkyl group with 5–7 carbon atoms.

7. A camptothecin derivative of the formula:

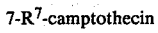

7-R$^7$-camptothecin wherein R$^7$ is a phenylalkyl group having 1 to 3 carbon atoms in the alkylene portion thereof.

8. A camptothecin derivative of the formula:

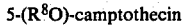

5-(R$^8$O)-camptothecin wherein R⁸ is a straight or branched chain alkyl group with 1-5 carbon atoms.

9. A camptothecin derivative of the formula:

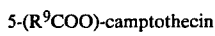
5-(R⁹COO)-camptothecin wherein R⁹ is a straight or branched chain alkyl group with 1-4 carbon atoms, phenyl or a phenylalkyl group having 1 to 3 carbon atoms in the alkylene portion thereof.

10. 5-Acetyloxy-20-O-acetylcamptothecin.
11. Camptothecin-7-carboxylic acid.
12. A camptothecin derivative of the formula:

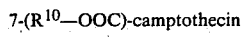
7-(R¹⁰—OOC)-camptothecin wherein R¹⁰ is a straight or branched chain alkyl group with 1 to 4 carbon atoms.

13. A process for the preparation of a camptothecin derivative of the formula:

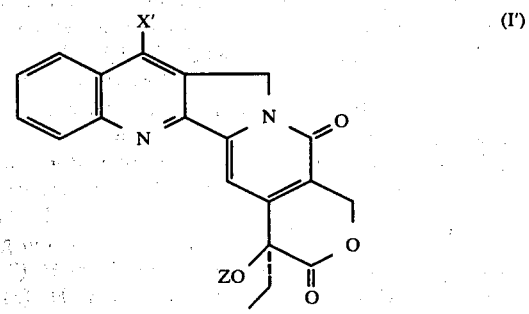
(I')

wherein X' is the group COOR⁴ or CH₂OR where R⁴ is H, lower alkyl or benzyl and R is H or R'CO where R' is a straight or branched chain alkyl group with 1-17 carbon atoms, trifluoromethyl, phenyl, a phenylalkyl group having 1 to 2 carbon atoms in the alkylene portion thereof or the group HOOC(CH₂)ₙ where n is an integer of 2 to 4, and Z is H, acetyl or trifluoroacetyl, or a water-soluble alkali metal salt thereof, which comprises subjecting camptothecin to a radical reaction with a hydroxymethyl compound of the general formula:

A—CH₂OH          (II)

wherein A is H, COOH or CH₂OH, by the aid of sulfuric acid and an inorganic or organic peroxide in an aqueous medium, the inorganic and organic peroxide being selected from the group consisting of hydrogen peroxide, persulfuric acid and ammonium and alkali metal salts thereof, Caro's acid and alkali metal salts thereof, alkali metal and alkaline earth metal peroxides, tert-butyl hydroperoxide, benzoyl peroxide and dialkanoyl peroxides.

14. A process according to claim 13, further comprising the step of treating the resultant 7-hydroxymethylcamptothecin with a compound of the formula:

R'COOH wherein R' has the same meaning as defined above, or an anhydride or acid halide thereof, to give the 7-R'COOCH₂ group wherein R' is as defined above with or without simultaneous acetylation or trifluoroacetylation.

15. A process according to claim 13, further comprising the step of oxidizing the resultant 7-hydroxymethyl-camptothecin with an oxidizer selected from the group consisting of chromium trioxide, alkali metal dichromates and permanganates to 7-carboxycamptothecin.

16. A process according to claim 14 or 15, further comprising the step of esterifying the 7-carboxyl group with a compound of the formula:

R⁴—OH wherein R⁴ has the same meaning as defined above, to form a 7-X"-camptothecin wherein X" is the group R⁴OCO— where R⁴ is as defined above.

17. A process according to claim 13, wherein the radical reaction is carried out in the presence of a metal ion supplied in the reaction medium from a transition metal salt selected from the group consisting of silver, iron (II), copper, cobalt, nickel, lead, mercury, cadmium, thallium and zinc salts in the form of halides, carbonates, nitrates, sulfates and acetates.

18. A process according to claim 17, wherein the transition metal salt is silver nitrate.

19. A process according to claim 17, wherein the transition metal salt is ferrous sulfate.

20. A process according to claim 13, wherein the peroxide is ammonium persulfate.

21. A process according to claim 13, wherein the peroxide is hydrogen peroxide.

22. A process according to claim 17, wherein the transition metal salt is used within the range from an almost equimolar amount to an about 30 molar amount with respect to the amount of camptothecin used.

23. A process according to claim 13, wherein the reaction is carried out at a temperature varying from room temperature to the boiling point of the reaction mixture.

24. A process according to claim 13, wherein the hydroxymethyl compound is methanol.

25. A process for the preparation of a camptothecin derivative of the formula:

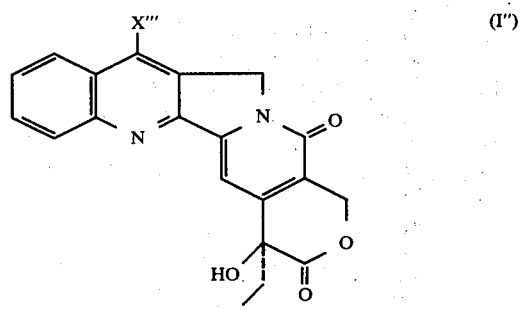
(I")

wherein X'" is a straight or branched chain alkyl group with 1-18 carbon atoms, a cycloalkyl group with 5-7 carbon atoms, a phenylalkyl group having 1 to 3 carbon atoms in the alkylene portion thereof, or the group —COOR⁴ where R⁴ is H or a lower alkyl group, or a water-soluble alkali metal salt thereof, which comprises subjecting camptothecin to a radical reaction with an organic compound of the general formula:

X"—Q          (II')

wherein Q is —CH₂OH, —COOH, —CHO, —COX" or

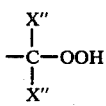

and X″ is a straight or branched chain alkyl group with 1–10 carbon atoms, a cycloalkyl group with 5–7 carbon atoms, or a phenylalkyl group having 1 to 3 carbon atoms in the alkylene portion thereof, by the aid of sulfuric acid and an inorganic or organic peroxide in an aqueous medium in the presence of a transition metal ion supplied in the medium from a transition metal salt selected from the group consisting of silver, iron (II), copper, cobat, nickel, lead, mercury, cadmium, thallium and zinc salts in the form of halides, carbonates, nitrates, sulfates and acetates, the inorganic or organic peroxide being selected from the group consisting of hydrogen peroxide, persulfuric acid and ammonium and alkali metal salts thereof, Caro's acid and alkali metal salts thereof, alkali metal and alkaline earth metal peroxides, tert-butyl hydroperoxide, benzoyl peroxide and dialkanoyl peroxides.

26. A process according to claim 25, further comprising the step of oxidizing the resultant 7-X″-camptothecin derivative wherein X″ is an alkyl group with an oxidizing agent selected from the group consisting of chromium trioxide, alkali metal dichromates and permanganates to a 7-X‴-camptothecin derivative wherein X‴ is a carboxy group.

27. A process according to claim 26, further comprising the step of esterifying the 7-carboxy group with a lower alkanol to form a 7-X‴-camptothecin wherein X‴ is a lower alkoxycarbonyl group.

28. A process according to claim 25, wherein the transition metal salt is silver nitrate.

29. A process according to claim 25, wherein the transition metal salt is ferrous sulfate.

30. A process according to claim 25, wherein the peroxide is ammonium persulfate.

31. A process according to claim 25, wherein the peroxide is hydrogen peroxide.

32. A process according to claim 25, wherein the organic compound is used in a large excess in molar ratio with respect to the camptothecin.

33. A process according to claim 32, wherein the organic compound is used in an amount of about 20 molar proportion with respect to the camptothecin.

34. A process according to claim 25, wherein the transition metal salt and the peroxide are used respectively in an amount of about 5 to 8 molar excess with respect to the camptothecin.

35. A process according to claim 25, wherein the peroxide is tert-butyl hydroperoxide.

36. A process for the preparation of a camptothecin derivative of the formula:

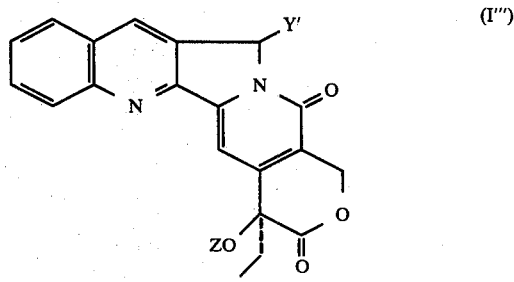

wherein Y′ is OH or the group OR$^3$ where R$^3$ is a lower alkyl group, a lower alkylcarbonyl group, benzoyl or a phenylalkyl group having 1 to 3 carbon atoms in the alkylene portion thereof, and Z is H or acetyl, or a water-soluble alkali metal salt thereof, which comprises treating camptothecin with sulfuric acid and a persulfate selected from the group consisting of ammonium persulfate, alkali metal persulfates, Caro's acid and alkali metal salts thereof in an aqueous medium containing a transition metal ion supplied in the medium from a transition metal salt selected from the group consisting of silver, iron (II), copper, cobalt, nickel, lead, mercury, cadmium, thallium and zinc salts in the form of halides, carbonates, nitrates, sulfates and acetates.

37. A process according to claim 36, further comprising the step of treating the resultant 5-hydroxycamptothecin with a compound of the general formula:

$$R^3-OH$$

wherein R$^3$ has the same meaning as defined above, to convert the 5-hydroxy group into a 5-R$^{3\prime}$O group where R$^{3\prime}$ is a lower alkyl group, or into a 5-R$^{3\prime\prime}$O group where R$^{3\prime\prime}$ is a lower alkylcarbonyl group, a benzoyl group or a phenylalkylcarbonyl group having 1 to 3 carbon atoms in the alkylene portion thereof, with or without simultaneous acetylation of the 20-hydroxy group.

38. A process according to claim 36 wherein the transition metal salt is silver nitrate.

39. A process according to claim 36, wherein the transition metal salt is ferrous sulfate.

40. A process according to claim 36, wherein the persulfate is used in an amount within the range of 5–30 molar proportion with respect to the camptothecin.

* * * * *